US011661582B2

(12) United States Patent
David et al.

(10) Patent No.: US 11,661,582 B2
(45) Date of Patent: May 30, 2023

(54) METHOD FOR PRODUCING SINOATRIAL NODE CELLS (PACEMAKER CELLS) FROM STEM CELLS, AND USE OF THE PRODUCED SINOATRIAL NODE CELLS

(71) Applicant: UNIVERSITAET ROSTOCK, Rostock (DE)

(72) Inventors: Robert David, Mering (DE); Julia Jung, Rostock (DE)

(73) Assignee: UNIVERSITAET ROSTOCK, Rostock (DE)

(*) Notice: Subject to any disclaimer, the term of this patent is extended or adjusted under 35 U.S.C. 154(b) by 101 days.

(21) Appl. No.: 15/106,388

(22) PCT Filed: Dec. 10, 2014

(86) PCT No.: PCT/EP2014/077215
§ 371 (c)(1),
(2) Date: Nov. 21, 2016

(87) PCT Pub. No.: WO2015/091157
PCT Pub. Date: Jun. 25, 2015

(65) Prior Publication Data
US 2017/0107494 A1 Apr. 20, 2017

(30) Foreign Application Priority Data
Dec. 20, 2013 (DE) .................. 10 2013 114 671.6

(51) Int. Cl.
C12N 15/85 (2006.01)
C12N 5/077 (2010.01)
C12N 5/10 (2006.01)
G01N 33/50 (2006.01)

(52) U.S. Cl.
CPC ............ C12N 5/0657 (2013.01); C12N 5/10 (2013.01); C12N 15/85 (2013.01); G01N 33/5061 (2013.01); C12N 2501/60 (2013.01); C12N 2506/02 (2013.01); C12N 2506/03 (2013.01); C12N 2506/04 (2013.01); C12N 2506/45 (2013.01); C12N 2510/00 (2013.01)

(58) Field of Classification Search
CPC .............. C12N 5/0657; C12N 2501/60; C12N 2506/02; C12N 2506/03; C12N 2506/04; C12N 2506/45; C12N 15/85
See application file for complete search history.

(56) References Cited

U.S. PATENT DOCUMENTS

2004/0096432 A1 5/2004 Fleischmann et al.
2013/0216503 A1 8/2013 Srivastava

FOREIGN PATENT DOCUMENTS

EP 2484756 A1 8/2012
JP 2013524837 A 6/2013
WO 2002051987 A1 7/2002
WO 2005108598 A1 11/2005
WO 2013/070952 A1 5/2013

OTHER PUBLICATIONS

Ho et al., Heart Rate and Electrocardiography Monitoring in Mice, Curr Protoc Mouse Biol, Mar. 1, 2011:1: 123-139.*
Spodick, Survey of Selected Cardiologists for an Operational Definition of Normal Sinus Heart Rate, The American Journal of Cardiology vol. 72, Aug. 15, 1993.*
International Search Report in International Application No. PCT/EP2014/077215, dated Jan. 22, 2015.
Rosen, M.R., Biological pacemaking: in our lifetime? Heart Rhythm., 2005. 2(4): pp. 418-428.
Ishii, T.M., et al., Molecular characterization of the hyperpolarization-activated cation channel in rabbit heart sinoatrial node. J Biol Chem., 1999. 274(18): pp. 12835-12839.
Stieber, J., F. Hofmann, and A. Ludwig, Pacemaker channels and sinus node arrhythmia. Trends Cardiovasc Med, 2004. 14(1): pp. 23-28.
Bakker, M.L., et al., T-box transcription factor TBX3 reprogrammes mature cardiac myocytes into pacemaker-like cells. Cardiovasc Res, 2012. 94(3): pp. 439-449.
Kapoor, N., et al., Direct conversion of quiescent cardiomyocytes to pacemaker cells by expression of Tbx18. Nat Biotechnol, 2013. 31(1): pp. 54-62.
Wiese, C., et al., Formation of the sinus node head and differentiation of sinus node myocardium are independently regulated by Tbx18 and Tbx3. Circ Res, 2009. 104(3): pp. 388-397 with supplement material.

(Continued)

Primary Examiner — Marcia S Noble
(74) Attorney, Agent, or Firm — Raphael Bellum PLLC

(57) ABSTRACT

The electrical pacemakers currently being used for the therapeutic approaches for treatment of "sick sinus syndrome" are not hormonally regulatable and entail risks through infections or premature battery discharge. These problems could be overcome by means of "biological cardiac pacemakers" obtained from pluripotent stem cells (PSCs). It has been shown that the controlled differentiation of stem cells with TBX, inductors of sinoatrial node cells, and an additional Myh6 promoter-specific antibiotic selection can give cardiomyocyte aggregates consisting to an extent of more than 80% of physiologically functional pacemaker cells. These induced sinoatrial bodies ("iSABs") for the first time exhibited very high beat frequencies (300-400 bpm), similar to those in a murine heart, and were able to stably rhythmically stimulate heart muscle cells ex vivo. In the iSAB transcriptome decoded by means of RNA-seq, it was possible to assign almost all the genes to the ontologies of heart function/heart development and the structures of contractile cells. Overall, this is the first example of a high-purity functional sinoatrial tissue derived from stem cells, which means that a crucial step for future cell therapy and the testing of medicaments in vitro is being implemented.

14 Claims, 36 Drawing Sheets

(56) References Cited

OTHER PUBLICATIONS

Nobus, A.M., G. Wallukat, and J. Hescheler, Pluripotent mouse embryonic stem cells are able to differentiate into cardiomyocytes expressing chronotropic responses to adrenergic and cholinergic agents and Ca2+ channel blockers. Differentiation, 1991. 48(3): pp. 173-182.

Kehat, I., et al., High-resolution electrophysiological assessment of human embryonic stem cell-derived jardiomyocytes: a novel in vitro model for the study of conduction. Circ Res, 2002. 91(8): pp. 659-661.

Kleger, A., et al., Modulation of calcium-activated potassium channels induces cardiogenesis of pluripotent stem cells and enrichment of pacemaker-like cells. Circulation, 2010. 122(18): pp. 1823-1836 with supplemental material.

Maltsev, V.A., et al., Cardiomyocytes differentiated in vitro from embryonic stem cells developmentally express cardiac-specific genes and ionic currents. Circ Res, 1994. 75(2): pp. 233-244.

David, R. and W.M. Franz, From pluripotency to distinct cardiomyocyte subtypes. Physiology (Bethesda), 2012. 27 (3): pp. 119-129.

Scavone, A., et al., Embryonic stem cell-derived CD166+ precursors develop into fully functional sinoatrial-like cells. Circ Res, 2013. 113(4): pp. 389-398.

David, R., et al., MesP1 drives vertebrate cardiovascular differentiation through Dkk-1-mediated blockade of Wnt-signalling. Nat Cell Biol., 2008. 10(3): pp. 338-345. Epub Feb. 24, 2008.

David, R., et al., Forward programming of pluripotent stem cells towards distinct cardiovascular cell types. Cardiovasc Res., 2009. 84(2): pp. 263-272. Epub Jun. 29, 2009.

Klug, M.G., et al., Genetically selected cardiomyocytes from differentiating embryonic stem cells form stable intracardiac grafts. J Clin Invest, 1996. 98(1): pp. 216-224.

David, R., et al., Selection of a common multipotent cardiovascular stem cell using the 3.4-kb MesP1 promoter fragment. Basic Res Cardiol, 2013. 108(1): 312.

Kensah, G., et al., Murine and human pluripotent stem cell-derived cardiac bodies form contractile myocardial tissue in vitro. Eur Heart J, 2013. 34(15): pp. 1134-1146.

Otsuji, T.G., et al., Progressive maturation in contracting cardiomyocytes derived from human embryonic stem cells: Qualitative effects on electrophysiological responses to drugs. Stem Cell Res, 2010. 4(3): pp. 201-213.

Kreuzberg, M.M., et al., Functional properties of mouse connexin30.2 expressed in the conduction system of the heart. Circ Res, 2005. 96(11): pp. 1169-1177 with online data supplements.

Verheijck, E.E., et al., Electrophysiological features of the mouse sinoatrial node in relation to connexin distribution. Cardiovasc Res, 2001. 52(1): pp. 40-50.

Halbach, M., et al., Ventricular slices of adult mouse hearts—a new multicellular in vitro model for electrophysiological studies. Cell Physiol Biochem, 2006. 18(1-3): pp. 1-8.

He, J.Q., et al., Human embryonic stem cells develop into multiple types of cardiac myocytes: action potential characterization. Circ Res, 2003. 93(1): pp. 32-39 with online supplement.

Yanagi, K., et al., Hyperpolarization-activated cyclic nucleotide-gated channels and Ttype calcium channels confer automaticity of embryonic stem cell-derived cardiomyocytes. Stem Cells, 2007. 25(11): pp. 2712-2719.

Barbuti, A., et al., Molecular composition and functional properties off-channels in murine embryonic stem cell-derived pacemaker cells. J Mol Cell Cardiol, 2009. 46(3): pp. 343-351.

Ma, J., et al., High purity human-induced pluripotent stem cell-derived cardiomyocytes: electrophysiological properties of action potentials and ionic currents. Am J Physiol Heart Circ Physiol, 2011. 301(5): pp. H2006-H2017.

Morikawa, K., et al., Identification, isolation and characterization of HCN4-positive pacemaking cells derived from murine embryonic stem cells during cardiac differentiation. Pacing Clin Electrophysiol, 2010. 33(3): pp. 290-303.

Garcia-Frigola, C., Y. Shi, and S.M. Evans, Expression of the hyperpolarizationactivated cyclic nucleotide-gated cation channel HCN4 during mouse heart development. Gene Expr Patterns, 2003. 3(6): pp. 777-783.

Wiese, C., et al., Differentiation induction of mouse embryonic stem cells into sinus node-like cells by suramin. Int J Cardiol, 2011. 147(1): pp. 95-111.

Johns, D.C., et al., Adenovirus-mediated expression of a voltage-gated potassium channel in vitro (rat cardiac myocytes) and in vivo (rat liver). A novel strategy for modifying excitability. J Clin Invest, 1995. 96(2): pp. 1152-1158.

Nuss, H.B., E. Marban, and D.C. Johns, Overexpression of a human potassium channel suppresses cardiac hyperexcitability in rabbit ventricular myocytes. J Clin Invest, 1999. 103(6): pp. 889-896.

Evans, M.J. and M.H. Kaufman, Establishment in culture of pluripotential cells from mouse embryos. Nature, 1981. 292(5819): pp. 154-156.

Martin, G.R., Isolation of a pluripotent cell line from early mouse embryos cultured in medium conditioned by teratocarcinoma stem cells. Proc Natl Acad Sci U S A, 1981. 78(12): pp. 7634-7638.

Gerecht-Nir, S., B. Fishman, and J. Itskovitz-Eldor, Cardiovascular potential of embryonic stem cells. Anat Rec A Discov Mol Cell Evol Biol, 2004. 276(1): pp. 58-65.

Takahashi, K. and S. Yamanaka, Induction of pluripotent stem cells from mouse embryonic and adult fibroblast cultures by defined factors. Cell., 2006. 126(4): pp. 663-676. Epub Aug. 10, 2006.

Takahashi, K., et al., Induction of pluripotent stem cells from adult human fibroblasts by defined factors. Cell., 2007. 131(5): pp. 861-872.

Mauritz, C., et al., Generation of functional murine cardiac myocytes from induced pluripotent stem cells. Circulation., 2008. 118(5): pp. 507-517. Epub Jul. 14, 2008.

David, R., M. Groebner, and W.M. Franz, Magnetic cell sorting purification of differentiated embryonic stem cells stably expressing truncated human CD4 as surface marker. Stem Cells, 2005. 23(4): pp. 477-482.

Trapnell, C., L. Pachter, and S.L. Salzberg, TopHat: discovering splice junctions with RNS-Seq. Bioinformatics, 2009. 25(9): pp. 1105-1111.

Anders, S. and W. Huber, Differential expression analysis for sequence count data. Genome Biol, 2010. 11(10): R106.

Goecks, J., A. Nekrutenko, and J. Taylor, Galaxy: a comprehensive approach for supporting accessible, reproducible, and transparent computational research in the life sciences. Genome Biol, 2010. 11(8): R86.

Hartung, S. et al. „Directing Cardiomyogenic Differentiation of Human Pluripotent Stem Cells by Plasmid-Based Transient Overexpression of Cardiac Transcription Factors, Stem Cells and Development, vol. 22, No. 7, 2013, pp. 1112-1125.

Halbach, M. et al. "Long-term persistence, functional integration and electrophysiological properties of transplanted cardiomyocytes derived from induced pluripotent stem cells" European Heart Journal, (Aug. 2013) vol. 34, Suppl. 1, S. 315. Meeting Info: European Society of Cardiology, ESC Congress 2013. Amsterdam, Netherlands Aug. 31, 2013-Sep. 4, 2013.

Barbuti et al., "Mesoangioblasts from ventricular vessels can differentiate in vitro into cardiac myocytes with sinotrial-like properties," J. Molec. Cellular Cardiol. 48, 2010, pp. 415-423.

Marger et al., "Pacemaker activity and ionic currents in mouse atrioventricular node cells," Channels, 5:3, 2011, pp. 241-250.

Jung et al., "Programming and Isolation of Highly Pure Physiologically and Pharmacologically Functional Sinus-Nodal Bodies from Pluripotent Stem Cells," Stem Cells Reports, vol. 2, 2014, pp. 592-605.

Marvin et al., "The Isolated Sinoatrial Node Cell in Primary Culture from the Newborn Rat", Circulation Research, vol. 55, No. 2, Aug. 1984 pp. 253-260.

\* cited by examiner

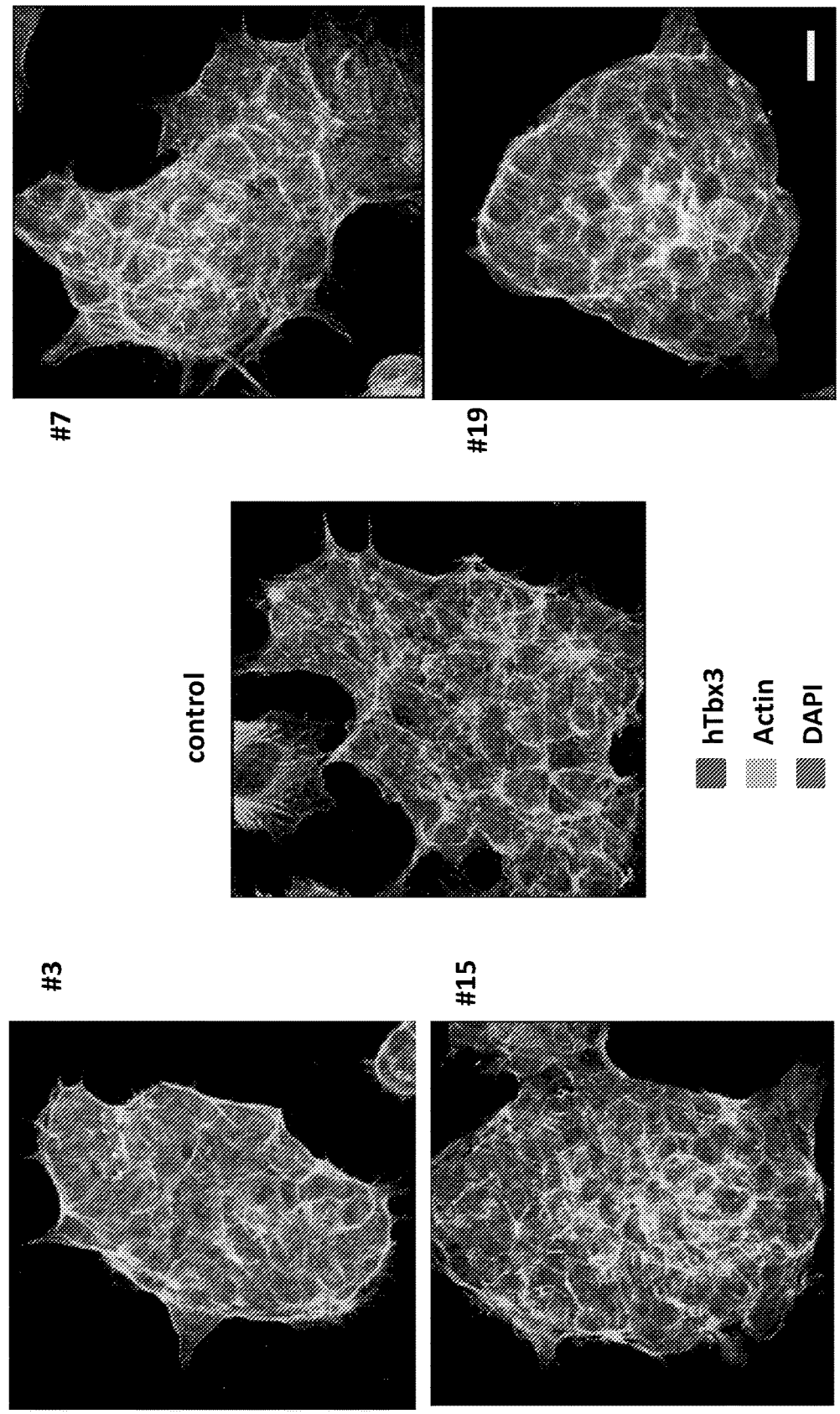

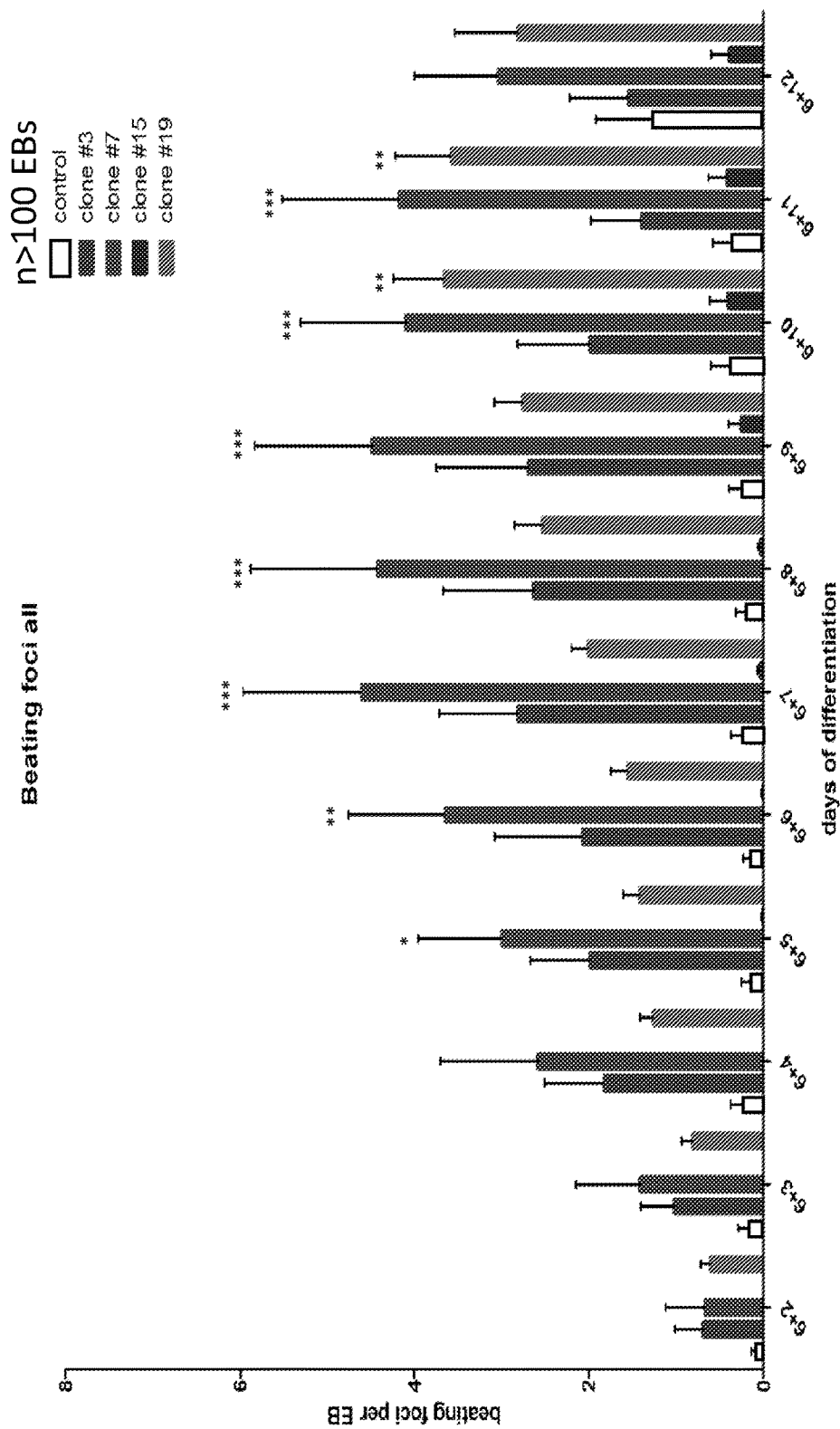

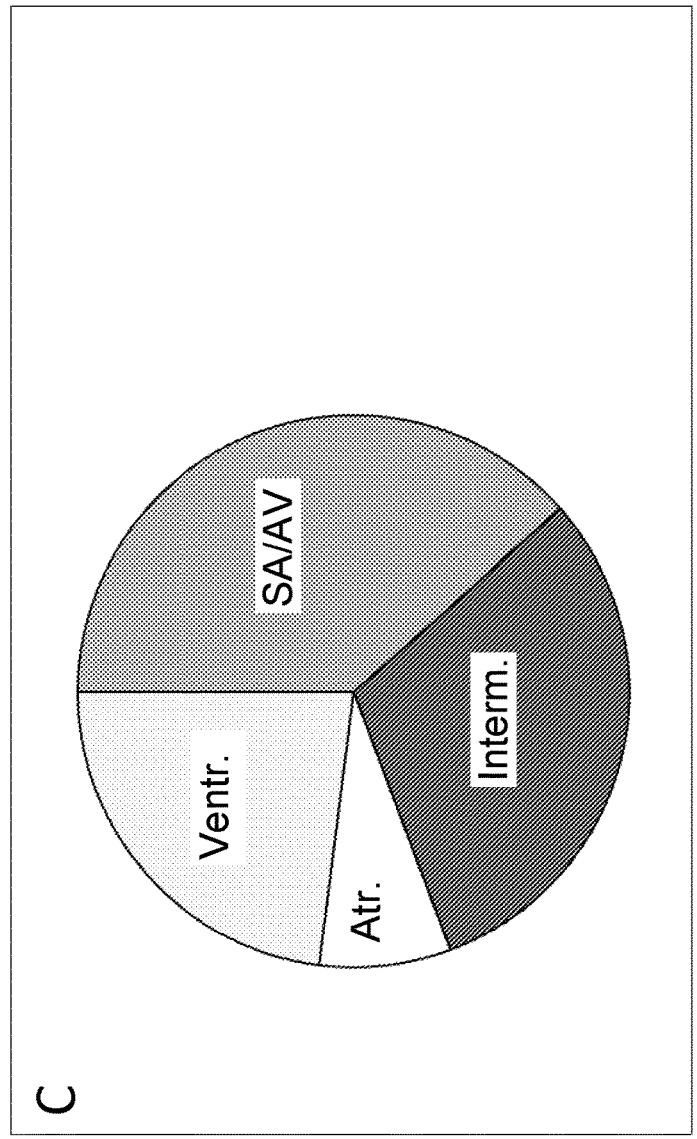
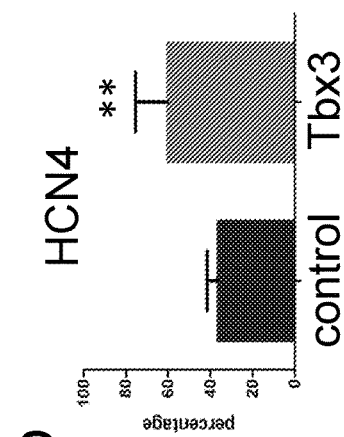
FIG. 2C

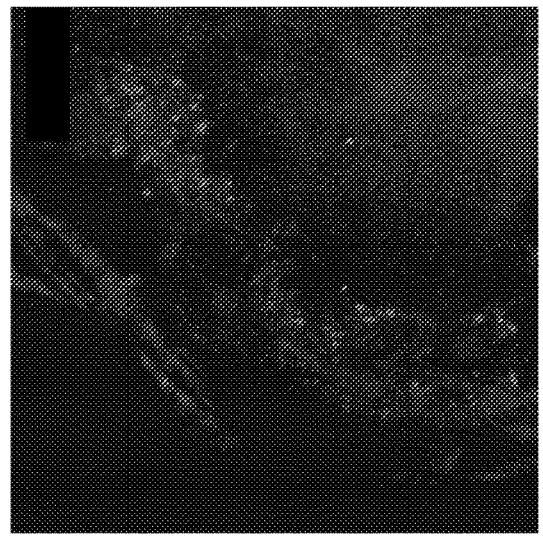
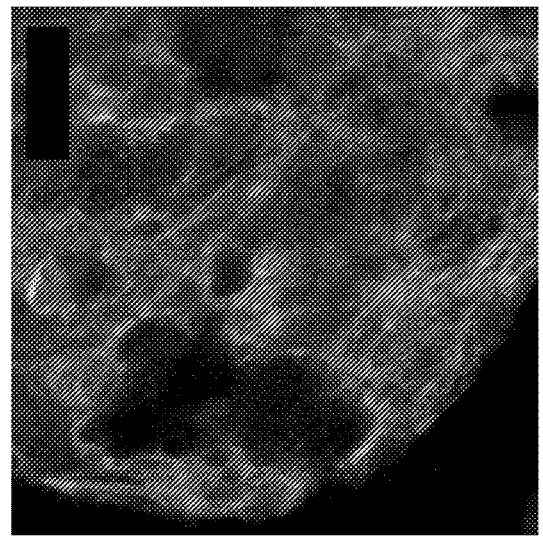
FIG. 3B

Spontaneous Ca²⁺-transients during inhibition of SR-Ca-ATPase

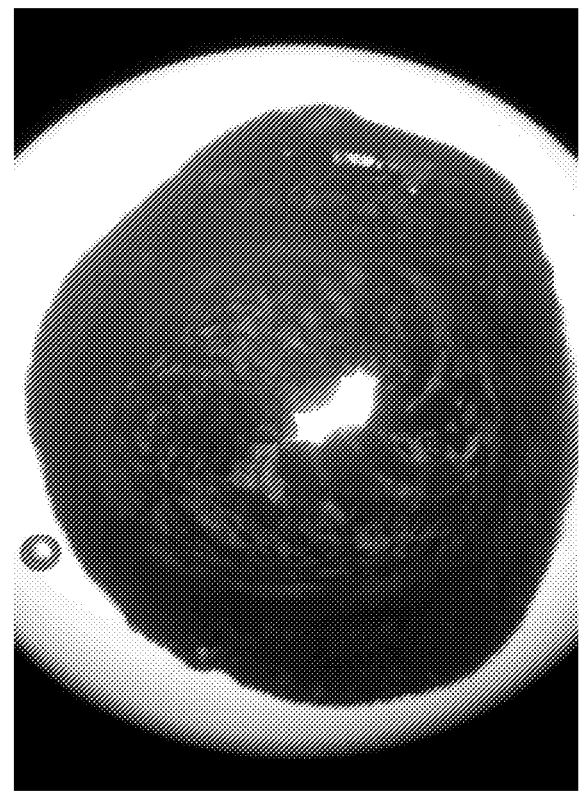
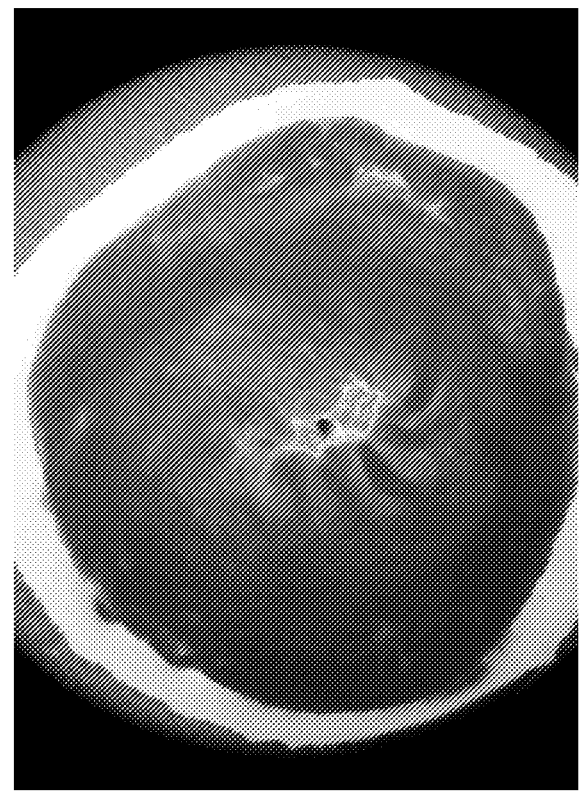
FIG. 4A

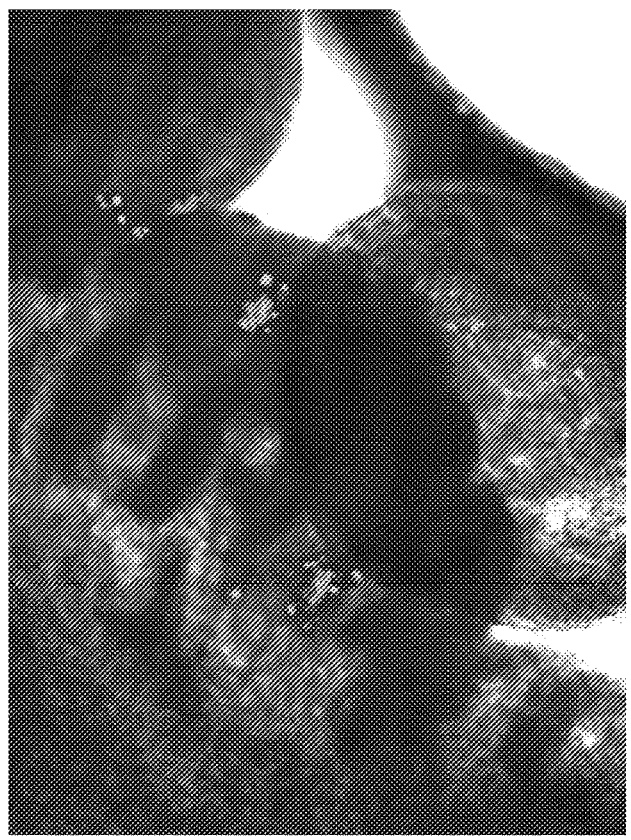
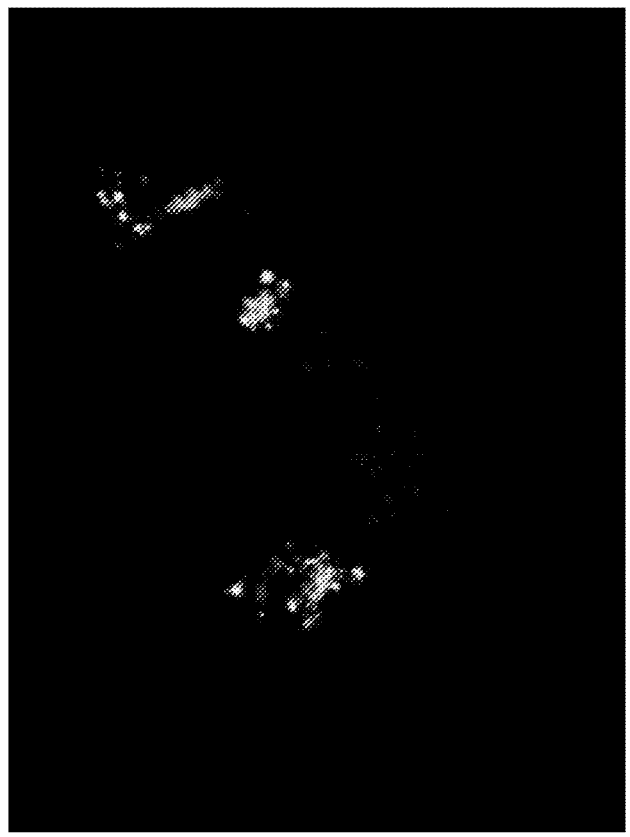
FIG. 4B

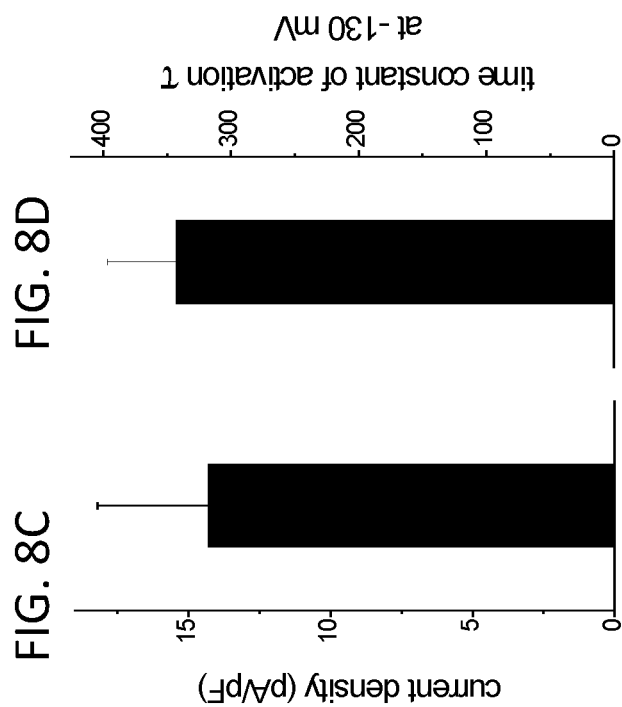
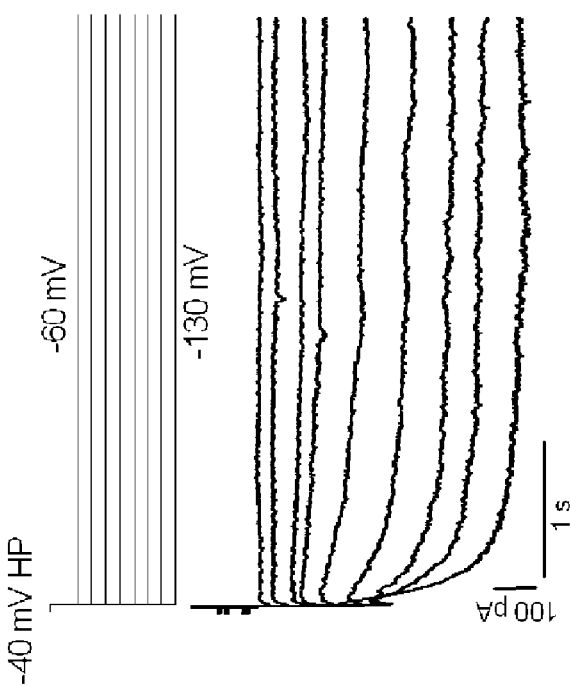

FIG. 10

Table 1

| AP-Typ | MDP (mV) | DDR (mV/s) | Overshoot (mV) | APD (ms) | Cyclelength (ms) | Plateau (ms) |
|---|---|---|---|---|---|---|
| Ventricular (n=9) | -50.2 ±11.75 | 37.9 ±31.20 | 35.8 ±5.83 | 319.2 ±134.90 | 896.2 ±552.54 | 164.5 ±108.40 |
| Atrial (n=3) | -53.9 ±4.78 | 31.5 ±14.7 | 40.6 ±0.1 | 165.9 ±66.6 | 650.6 ±296.7 | 78.5 ±48.0 |
| Pacemaker system (n=15) | -47.9 ±4.8 | 105.0 ±37.6 | 20.5 ±10.7 | 203.6 ±96.1 | 342.2 ±130.2 | -- |
| Intermediate (n=12) | -50.5 ±6.18 | 87.7 ±35.4 | 30.5 ±14.6 | 210.4 ±98.4 | 378.7 ±123.3 | 66.4 ±29.5 |

FIG. 11

Table 2

| AP-Typ | MDP (mV) | DDR (mV/s) | Overshoot (mV) | APD (ms) | Cyclelength (ms) | Plateau (ms) |
|---|---|---|---|---|---|---|
| Mat. Pacemaker system (n=43) | -54.7 ±3.7 | 116.7 ±85.3 | 21.6 ±7.6 | 86.2 ±28.2 | 197.4 ±63.2 | -- |
| Early Pacemaker (n=10) | -60.4 ±3.5 | 108.8 ±102.0 | 28.7 ±24.1 | 114.5 ±97.4 | 263.3 ±154.7 | 33.7 ±32.6 |

METHOD FOR PRODUCING SINOATRIAL NODE CELLS (PACEMAKER CELLS) FROM STEM CELLS, AND USE OF THE PRODUCED SINOATRIAL NODE CELLS

The term "sick sinus syndrome" is used as a collective term for the description of a series of disorders that are caused by disrupted function of the sinoatrial node, the pacemaker of the heart. In terms of structure, it is formed from specialized cardiomyocytes which are innervated by the autonomic nervous system. The disorders include pathological symptomatic sinus bradycardia, SA block (SA=sinoatrial), sinus arrest and tachycardia-bradycardia syndrome.

Sick sinus syndrome is frequently accompanied by general cardiac disorders such as ischemic heart disease, cardiomyopathy or myocarditis. These lead either to disrupted development of action potentials within the sinoatrial node or to disrupted conduction of electrical pulses from the sinoatrial node to the atrium (the latter being referred to as "sinoatrial conduction disorder"). At present, therapeutic measures for "sick sinus syndrome" are based on the implantation of artificial pacemakers which are extremely costly and have no sensitivity to hormonal stimulation. An additional factor is that risks resulting from infection and premature battery discharge lead to crucial restrictions. Thus, patients having an implanted pacemaker are generally subject to a high risk of serious complications in their remaining lifetime.

These defects could be avoided by the availability of functional SA node cells (synonyms: sinoatrial node cells, node cells, cardiac pacemaker cells) for transplants or by their de novo production in vivo. Node cells are characterized by their low membrane potential, diastolic depolarization and low upstroke rates. Several different ion currents are involved in diastolic depolarization and the action potentials in the SA node, including the pacemaker current $I_f$. This current is carried by the HCN channels regulated by cyclic nucleotides. The cAMP binding site in the HCN channel enables the modulation of the activation by catecholamines, and this property could control the autonomic regulation of the pacemaker mechanism [1]. The isoforms of the channel, referred to as HCN1 to HCN4, are encoded by four genes. By far the predominant isoform in the SA node is HCN4 [2] [3].

In order to obtain biological pacemaker cells for future therapies, two approaches have been pursued:

On the one hand, the aim is to transform beating heart muscle cells in situ by means of a genetic manipulation to cardiac pacemaker cells ("direct reprogramming"). In this connection, TBX3, a fundamental early transcription factor, led to cells having incomplete pacemaker properties [4]. Recently, it was reported that viral overexpression of Tbx18, a member of the same transcription factor family, enabled the reprogramming of ventricular myocardium to sinoatrial node cells [5]. However, this procedure requires viral vectors, which prevents spatial and time-regulatable expression of the reprogramming factor for simulation of the in vivo situation of the developing embryo. Furthermore, the efficiency was very low [5]. In addition, it has been shown that Tbx18 is expressed only transiently in the head portion of the evolving sinoatrial node, whereas the Tbx3 factor which is used here (i.e. in the inventive approach) for the controlled differentiation, by contrast with direct reprogramming, is expressed permanently in vivo in the whole sinoatrial node [6].

A further approach is based on the transplantation of "biological pacemakers" produced in vitro, which have been obtained from pluripotent stem cells (stem cell=S cell or SC) such as embryonic stem cells (ESCs or ES cells) or induced pluripotent stem cells (iPSCs) [7][8]. In this connection, it has been postulated that the low molecular weight compound EBIO enhances the formation of node cells from murine ES cells to a certain degree [9]. However, the publication does not address the actual ability of the cells to stimulate ventricular cardiac muscle cells, and the beat frequencies of the cells were likewise (too) low. In addition, at the electrophysiological level, no distinction was made between relatively mature pacemaker cells and the likewise spontaneously contracting early/intermediate cell type [9] [10] [11].

It has recently been reported that sinoatrial node cells can arise from a cell population purified via the detection of Alcam expression (CD166). However, applicability to the human system is not clear here, since the specificity of surface markers between the species is frequently not conserved [12].

It was therefore an object of the present invention to provide cardiac pacemaker cells (sinoatrial node cells) having improved pacemaker properties which have been obtained in vitro from stem cells and in a high yield.

This object was achieved by a method as claimed in claim 1. Further preferred embodiments are disclosed in the dependent claims. In other words, this object was achieved by a method of producing sinoatrial node cells ("cardiac pacemaker cells") from stem cells, in which a nucleic acid is introduced into stem cells, as a result of which these express a TBX transcription factor, or a TBX protein is introduced into the stem cells, wherein the method is characterized in that a construct for expression of an antibiotic resistance gene which is controlled by an alpha-MHC (MYH6) promoter is additionally introduced and the resulting stem cells are differentiated in the presence of the antibiotic. "Resulting stem cells" means stem cells which include both TBX (nucleic acid or protein) and the construct.

This constitutes a further-developed type of alternative of the controlled differentiation of ES cells recently introduced by the inventors to give specific cardiomyocyte subtypes via individual transcription factors [13] [14] [11]. It is a "type of alternative" because the focus has to date been on other subtypes.

By the application of the procedure, i.e. controlled differentiation via individual transcription factors, to TBX, especially TBX3, it has been shown that this already leads to doubling of functional pacemaker cells. However, this is still insufficient to obtain pure populations of these cells. This correlates with the inability of TBX3 to accomplish functional reprogramming as a single factor [4].

According to the invention, therefore, the method was combined with an antibiotic selection based on the Myh6 promoter [15]. This afforded cell aggregates which consisted exclusively of spontaneously beating cardiomyocyte cells (KM cells) and which had a beat frequency which, for the first time, was close to that of a (murine) heart.

Of these cells, more than 60%, especially more than 70%, most preferably more than 80%, exhibited the desired type of pacemaker cells (based on the cardiomyocyte subtypes produced) having full functionality at the levels of protein expression, electrophysiological parameters and $Ca^{2+}$ transients, and also potency thereof for stable ex vivo stimulation of cardiac muscle cultures, especially murine cardiac muscle cultures. Some of literature already mentions a 60% yield, but it does not mention that no distinction was made between early/intermediate cells and differentiated pacemaker cells. The former also beat spontaneously—like cardiac pacemaker cells—but otherwise have different properties that make them unsuitable as cardiac pacemaker cells (i.e. they are at the start of differentiation and can/will still give rise to all subtypes, i.e. not only pacemaker cells but also atrial and ventricular cells).

The cells or cell aggregates obtained in accordance with the invention, which are also referred to as "induced sinoatrial bodies" (iSABs), were additionally analyzed with respect to their entire mRNA expression pattern using RNA-seq, which confirmed the results. Thus, the invention results in highly enriched populations of pacemaker cells which have been derived from stem cells, these having all the properties that are characteristic of this cell type, which will have great significance for future cell therapy and in vitro evaluation of medicaments.

If a nucleic acid is introduced into the stem cells for expression of a TBX transcription factor, this is preferably selected from TBX DNA, especially TBX cDNA; or TBX RNA, especially TBX mRNA. In the context of RNA, TBX mRNA can be transfected into the stem cells, although this does not give a stable gene modification. Alternatively, it is possible to introduce micro-RNAs which result in expression of endogenous TBX. In a preferred embodiment of the nucleic acid introduction, TBX DNA, especially TBX cDNA, is introduced by means of vector, especially by means of an (over-)expression vector. The TBX is preferably selected from TBX3 or TBX-18, particular preference being given to TBX3 and greatest preference to TBX3 cDNA. In other words, a most-preferred variant is the introduction of TBX3 cDNA with overexpression vector. With regard to the TBX protein, which likewise does not cause a (stable) gene modification, TBX3 is preferred.

Human or nonhuman nucleic acids or proteins are used, preference being given to those of human origin.

With regard to the stem cells used, multipotent or pluripotent, preferably pluripotent, stem cells are used. The stem cells may be selected from human or nonhuman embryonic stem cells or human or nonhuman induced stem cells or human induced stem cells or parthenogenetic stem cells or spermatogonial stem cells. They are preferably nonhuman embryonic stem cells or nonhuman induced stem cells or human induced stem cells or parthenogenetic stem cells or spermatogonial stem cells, more preferably nonhuman embryonic stem cells or nonhuman induced stem cells or human induced stem cells. Human embryonic stem cells are explicitly excluded in the preferred and particularly preferred variant.

The antibiotic selection of the invention on the basis of the Myh6 promoter preferably utilizes an antibiotic resistance gene selected from aminoglycoside antibiotic resistance gene, more preferably from neomycin and puromycin resistance gene, most preferably neomycin resistance gene. The antibiotic used for selection is correspondingly selected from aminoglycoside antibiotic, especially from neomycin and puromycin. "Correspondingly selected" means that it is always the antibiotic corresponding to the resistance gene that is used; for example, in the case of the neomycin resistance gene, there is subsequent selection with neomycin.

What are produced in each case are cardiac pacemaker cells (human or nonhuman), preference being given to human cardiac pacemaker cells. For this purpose, human stem cells are combined with preferably human protein or human nucleic acid. Cross-combinations, for example the introduction of human proteins or human nucleic acid into nonhuman, for example murine, stem cells are likewise possible, as is the pure combination of the nonhuman representatives for production of nonhuman cardiac pacemaker cells.

As will be elucidated in detail hereinafter, sinoatrial node cells of the invention that have been produced in vitro from stem cells (also synonymous in shortened form: inventive sinoatrial node cells or sinoatrial node cells produced in accordance with the invention from stem cells), when contacted with pharmaceuticals, show the expected behavior: for example, both the HCN channel blocker ZD-7288 and the muscarinic receptor antagonist carbachol cause a significant reduction in beat frequency. The administration of the β-adrenoreceptor agonist isoprotenerol, by contrast, leads to an increase in beat frequency. Since the sinoatrial node cells of the invention that have been produced from stem cells reacted to the pharmaceuticals administered in just the same way as sinoatrial node cells in vivo, they are suitable as a model for normal sinoatrial node cells. Sinoatrial node cells produced in vitro from stem cells, especially the sinoatrial node cells produced in accordance with the invention (in vitro) from stem cells, are therefore also used, inter alia, for in vitro evaluation of medicaments. This is understood to be synonymous with the study of active ingredients, i.e. potential medicaments, for the actual suitability as such ("in vitro drug testing"). Potential candidates for novel medicaments have to be tested in mandatory preclinical and clinical studies for their quality, safety and efficacy before they are approved for the market by the medicament authorities. Since the biochemical and chemoinformatic preliminary studies have to date not given any final certainty as to how a novel active ingredient behaves in vivo, novel active ingredients have to be tested in preclinical studies, which has to date made animal experiments on a large scale indispensable. The use of sinoatrial node cells produced in vitro from stem cells, especially of the sinoatrial node cells of the invention, can at least help to reduce the extent of animal experiments. It is likewise possible to use sinoatrial node cells produced in vitro from stem cells, especially the sinoatrial node cells of the invention, at the early preclinical stage, since cell-based in vitro assays can often also be used in the search for active ingredient candidates and in studying toxicity, because of the fact that these essential aspects can be reflected in vivo pharmacology and toxicology.

Sinoatrial node cells produced in vitro from stem cells, especially the sinoatrial node cells produced in accordance with the invention from stem cells, can be used for construction of cardiac tissue and/or growing of cardiac tissue, especially for implementation purposes, but also for de novo production in vivo. More particularly, the focus here is on the production of cell-based biological cardiac pacemakers.

The studies underlying the invention are presented in detail hereinafter:

Production of Stable TBX3-Overexpressing ES Cell Lines

On the basis of the high conservation of the TBX3 proteins in vertebrates, human TBX3 was inserted into murine ES cells because its specific detectability here is high. For overexpression in ES cells, human TBX3-cDNA was inserted into pEF-DEST51 (Invitrogen). From 20 independent clones, four clones which represent the entire spectrum from a low to a high degree of TBX3 mRNA overexpression were selected on the basis of the results from the qRT-PCR (FIG. 1A). This overexpression level was confirmed at the protein level (FIG. 1B). In FACS analyses, no pointer to any influence of the TBX3 overexpression on the percentage of the pluripotency markers Oct-4/Pou5f1-positive and Sox2-positive cells was found (FIG. 1C). This corresponds to normal undifferentiated colony growth in a LIF-containing medium (FIG. 1B) and is in agreement with the results obtained previously for MESP1 and NKX2-5 overexpression [13] [14] [11]. It was concluded from this that, analogously to these factors, TBX3 alone does not have the potency to induce differentiation of ES cells.

Effect of TBX3 Overexpression on Yield and Subtypes of the Spontaneously Beating Cardiomyocytes Derived from ES Cells ES cell clones having high and moderate TBX3 overexpression began to contract earlier during the differentiation and showed about 5 to 10 times the number of contracting areas (FIG. 2A). This increased cardiac differentiation is similar to the effect of MESP1 and NKX2-5 overexpression, which was described recently by the inventors [13] [14] [11]. In accordance with their enhanced beat activity, TBX3-overexpressing cardiomyocytes showed normal expression patterns of the sarcomeric marker Myh6 (FIG. 2B).

For the further validation of the functionality and determination of the proportions of the subtypes of the cardiomyocytes, the electrophysiological properties were analyzed by the single-cell patch-clamp technique and the measurement of the density of the HCN (or funny) channels on day 18 of the differentiation as described [13] [14] [16].

Generally speaking, all the subtypes described of isolated beating cardiomyocytes that are obtained during EB development are present in the preparations of the TBX3 cell clones, namely ventricular, atrial and SA/AV (pacemaker-type) cells, and also early/intermediate cells (FIG. 2C; additional table 1). The action potentials generated by the different cell types do not differ significantly between the TBX3 cells and the control cells in terms of their individual parameters, for instance MDP, DDR, upstroke rate and the duration of the AP plateau phase or in relation to their reaction to β-adrenergic (isoproterenol) or muscarinic (carbachol) stimulation, which supports the assumption of correct development of cardiomyocytes (FIG. 2C; additional table 1). However, an unusually high proportion of the pacemaker-type subtype was found in the TBX3-overexpressing cells, which constituted 38.5% of all the cardiomyocytes. These cells did not have a plateau phase, had a high density of funny channels ($I_f$) and a positive MDP of $>-60$ mV and exhibited the highest DDR values, which normally exceed 60 mV/s. By contrast, they had the slowest upstroke rate and the quickest depolarization rate ($<5$ V/s) and the smallest positive overshoot with a maximum of +10 mV. In addition, the SA/AV cells reacted as expected to isoproterenol, which led to an acceleration in the AP rate. In accordance with the high proportion of pacemaker cells in the cardiomyocytes selectively differentiated by TBX3, the number of cells that express the HCN4 channel, corresponding to the "funny channel", was increased (FIG. 2D).

In order to further increase the yield of the SA/AV subtype which was obtained via controlled differentiation by means of TBX3, an attempt was made to combine this method with an antibiotic selection based on the Myh6 promoter [15], since it was recently stated that the latter method enriches pacemaker cells in particular [17] [18], but with a very unsatisfactory yield of not more than 40%.

For this purpose, the plasmid containing the Myh6-neomycin cassette [15] was additionally inserted into the TBX3 clone. The administration of the antibiotic (neomycin) during the differentiation lead, as expected, to an enrichment of beating tissue in the control cells obtained by Myh6 promoter-assisted antibiotic selection (but without Tbx3), which were referred to as antibiotic-selected cardiac bodies ("aCaBs"). In the same way, the double-transgenic Myh6-TBX3 clones were enriched to spontaneously contracting areas. However, in the case of the latter, the beat rate of the correspondingly beating cells was virtually doubled (FIG. 3A). After the introduction of additional dissociation step, a further increase in beat rate was obtained both in the antibiotic-selected Myh6 promoter control cells and in the double-transgenic Myh6-TBX3 cell clones. In the case of the latter cells, for the first time, cell aggregates that contracted at 300-400 bpm were obtained, which is close to the beat frequency of murine hearts (~500 bpm) and suggests the formation of "induced sinoatrial bodies" (iSABs) (FIG. 3A). The cells within the iSABs were positive for HCN4 and for the connexins Cx45 and Cx30.2 (FIG. 3B), which is characteristic of pacemaker cells [19, 20].

The further cultivation of the iSABs for three weeks with gelatin-based cell culture dishes led to accumulated, highly synchronized cell layers that beat at >350 bpm. The cells had the typical elongated form of sinoatrial node cells auf (FIG. 3C).

To study the electrophysiological parameters of the cardiomyocytes derived from the iSABs, again, the single-cell patch-clamp technique was used. Of the 65 cells analyzed, 53 cells (81.5%) now corresponded to the regularly and rapidly beating subtype of the pacemaker cells and only 12 cells (18.5%) represented the irregularly and slowly beating myocardial subtype. In addition, 43 of the 53 cells classified as a subtype of the pacemaker cells exhibited parameters of mature pacemaker cells, while 10 of these regularly and spontaneously beating cells were still immature (FIG. 3D, additional table 2). Even though they have a short plateau phase and a more negative MDP, which distinguishes them from mature pacemaker cells, they do, however, already exhibit the typical features of pacemaker cells such as the generation of regular spontaneous action potentials with a rapid DDR and have a typical pacemaker current $I_f$ (see, for example, the derivations in FIG. 3B).

For further evidence of their identity with pacemaker cells, the $Ca^{2+}$ current from the extracellular space and the intracellular $Ca^{2+}$ stores were characterized, which is imparted by the $Ca^{2+}$ channels in the sarcolemma or by the release of $Ca^{2+}$ from the stores. The physiological functionality of the channels within the sarcolemma also determines the frequency of the $Ca^{2+}$ transients. As a feature of pacemaker cells, the cells were examined for HCN channels which modulate the frequency of the $Ca^{2+}$ transients. The administration of the HCN channel blocker ZD 7288 reduced the frequency of the $Ca^{2+}$ transients in the iSABs as a function of time (FIG. 3E). In addition, the frequency of the $Ca^{2+}$ transients is likewise based on the activity of the voltage-dependent T-type and L-type $Ca^{2+}$ channels. Correspondingly, the spontaneous frequencies of the $Ca^{2+}$ transients in the cells derived from iSAB are dramatically reduced after inhibition of the L-type $Ca^{2+}$ channels with nifedipine and the inhibition of the T-type $Ca^{2+}$ channels with mibefradil led to a moderate decrease (FIG. 3F).

A functional sarcoplasmic reticulin (SR) identifies the maturity stage of the cardiomyocytes. Thus, the $Ca^{2+}$ from the SR plays a crucial role for the spontaneous activity. This influence of the $Ca^{2+}$ which originates from the SR on spontaneous $Ca^{2+}$ transients becomes clear when full release of $Ca^{2+}$ from the SR is induced with caffeine, or inhibition of SERCA with thapsigargin. In the cells derived from iSABs, the caffeine-induced $Ca^{2+}$ release from the SR increased the diastolic $Ca^{2+}$ level in a comparable manner to a $Ca^{2+}$ peak, but with recognizable spontaneous $Ca^{2+}$ transients over the course of the $Ca^{2+}$ peak and with unchanged systolic $Ca^{2+}$ values (FIG. 3G). No similar caffeine-induced effect on the SR-$Ca^{2+}$ release can be detected in the cells derived from aCaBs. The blockage of the reuptake of $Ca^{2+}$ into the SR by thapsigargin resulted in an increase in the $Ca^{2+}$ diastolic level only in the cells derived from iSABs (FIG. 3H).

The predominant proportion of the $Ca^{2+}$ underlying the $Ca^{2+}$ transients originates from the extracellular space. Therefore, exchange of the extracellular $Ca^{2+}$ leads to elimination of the $Ca^{2+}$ transients. When the sarcolemmal $Ca^{2+}$ influx is eliminated by the blockage of the $Na^+/Ca^{2+}$ exchanger and the $Ca^{2+}$ channels, only an intracellular $Ca^{2+}$ circuit can be detected. In this case, the addition of caffeine induced a $Ca^{2+}$ peak in the cells derived from iSABs, this peak being four times greater compared to the cells derived from aCaBs (FIG. 3 I, K). The additional inhibition of the SERCA under these conditions revealed a leak in the SR in the cells derived from iSABs. The rate of intracellular $Ca^{2+}$ accumulation is subject to a fourfold increase compared to the management without SERCA inhibition. The addition of caffeine 5 min after the incubation with thapsigargin reduced the $Ca^{2+}$ peak by a factor of 4. By contrast, in the control cells, the $Ca^{2+}$ peak remained identical with and without SERCA inhibition (FIG. 3 J, K), and it was also impossible to detect any intracellular $Ca^{2+}$ accumulation.

In order ultimately to examine the iSABs for functional pacemaker activity, the advantages of an ex vivo model based on cultivated ventricular slices of murine hearts were utilized [21] (FIG. 4A). While these normally have spontaneous beat activity immediately after preparation, it is possible to induce a stable contraction therein down to ~60 bpm, and as such they constitute an ideal test system for the functionality of the iSABs produced. As apparent from the labeling with DiI, the iSABs sown on the slices were capable of adhering to the slices and surviving thereon (FIG. 4B). In order to determine the effect of the sowing of the iSABs, the spontaneous slice activity was first carefully quantified in naive slices. After a maximum of 70% of the slices contained at least one area with spontaneous beat activity on day 2 after the slice preparation, this percentage decreased dramatically on days 3 and 4 (FIG. 4C). While the slices sown with iSABs, by contrast with those sown with aCaBs, already exhibited a ~1.5-fold increase in beat activity on days 1 and 2, it was exclusively their activity that was also maintained thereafter (FIG. 4C). In addition, the slices on day 3 and day 4 contained significantly more very active regions per slice compared to the unsown and aCaB-sown slices (FIG. 4 D). In addition, the beat frequencies of the slices sown with iSAB increased continuously and significantly by more than 4 times from day 1 to day 4 (FIG. 4E); this was not observed in the case of the unsown and the aCaB-sown slices (dns). The loading of the iSABs with calcein prior to the transfer to the slices confirmed the formation of syncytia between the iSAB and the ventricular cells, as apparent from the plot of the dye against time (FIG. 4F). In addition, the functional coupling is apparent from the synchronized $Ca^{2+}$ transients between iSABs and the myocardial cells of the slice. As a result, the peaks of the $Ca^{2+}$ transients within the slice are smaller, but are highly synchronous with the spontaneous iSAB activity and can be detected within a radius of ~200 μm (FIG. 4G).

Finally, the global status of the transcriptome of the iSABs was ascertained by means of RNA sequence analyses with the aim of identifying novel factors and/or markers that are of significance for the pacemaker production. By means of this analysis, by comparison with the controls, 220 significantly upregulated genes were identified in the iSABs. Among these were Myh6 (33-fold upregulation), SERCA2 (20-fold upregulation), Ryr2 (39-fold upregulation) and Kcnj5 (45-fold upregulation). Overall, it was possible to assign the upregulated genes to 82 gene ontologies that describe biological processes (FIG. 5A). Among these, it was possible to classify the predominant number into groups that are (extremely) closely connected to heart and muscle functions and heart development (FIG. 5B). The underlying network of gene ontologies is shown in FIG. 5C. In the addressing of cellular components, the 220 genes divide into 34 ontologies (FIG. 5D). Equally, they could be classified into groups associated to a high degree with structures typical of contractile cells (FIG. 5E). The underlying network of gene ontologies is shown in FIG. 5F. Interestingly, almost 12 times more genes (>2500) in the iSABs were significantly downregulated, which possibly correlates with the role of TBX3 as a transcriptional repressor. However, these genes were connected more to ontologies that are relevant for housekeeping processes, for instance the signal cascades of G protein-coupled receptors and mitochondrial function.

4. Discussion

The capacity for de novo production of highly enriched populations of cardiac pacemaker cells obtained from stem cells, all of which incorporate functional parameters of mature sinoatrial node cells, is of great interest for future cell-based therapies. This may be a contributing factor in restoring proper heart rhythm in the manner of a "biological pacemaker". In addition, in vitro medicament screening will profit from the availability of such purified node cells. Pluripotent stem cells (PSCs) are at the focus of these aims, since it has been demonstrated for these that any cell type in the mammalian organism can form therefrom, including spontaneously beating cardiomyocytes having the molecular and functional properties that are characteristic of SA cells/pacemaker cells [10] [22] [23] [24] [25] [11]. However, the cell populations in "embryoid bodies" are typically extremely heterogeneous, the inevitable effect of which is that reliable selection and isolation strategies are required—this relates particularly to the very rare type of cardiac sinoatrial node cells. In this connection, cells derived from murine ES cells have been described, which incorporate EGFP transcriptionally controlled by the promoter of the HCN4 gene, which co-express EGFP, HCN4 and other cardiac markers in spontaneously beating areas [26]. However, after purification by flow cytometry, spontaneous action potentials were observed only rarely in the EGFP-positive fraction and, interestingly, most cells were positive for nestin, a marker of neurons [26]. This is in accordance with the knowledge that HCN4 is both a marker for spontaneous active cardiomyocytes and for nerve cells [27]. As a result, as an alternative to this, the search for endogenous surface markers for purification of these very sought-after cells was expedited. In this connection, it has recently reported that a purification based on Alcam (CD166) improves the content of node cells. As apparent from the staining of HCN4, the enrichment of the desired cell type, however, did not even exceed 10% in the resulting cells obtained from the ES cell culture. With regard to the cells, it was reported that they are capable of stimulating contractions in ventricular cardiomyocytes cultivated in vitro, but these important results were not presented in the publication [12].

Other approaches attempted to achieve the increase in the yield of node cells from differentiating ESCs via the pharmacological administration of low molecular weight compounds. Even though certain successes (a 3-6-fold increase) have been reported, this by no means gave sufficiently high enrichment of functional sinoatrial node cell populations [28]. Equally, in a publication relating to the administration of the low molecular weight compound EBIO which describes an increase in the proportion of node cells, there is a lack of comprehensive analyses at the electrophysiological and functional level [9].

In order to overcome this problem, a protocol which combines programming for controlled differentiation of ES cells using TBX, especially TBX3, as an important transcription factor was combined with a Myh6-assisted antibiotic selection was developed [15]. This consistently led to very effective production of sinoatrial node-like pacemaker cell aggregates which are characterized by spontaneously contracting cardiomyocytes having highly synchronized beat frequencies of 300 to 400 bpm, which for the first time come close to the frequencies in a murine heart. Most (>80%) of the cardiomyocytes in these cell clusters clearly represent the desired type of node cell—no purities anywhere near these have been achieved before [9] [28] [12]. Since the cells produced have all other properties for full functionality, i.e. protein expression patterns, electrophysiological and $Ca^{2+}$ signal parameters, it is proposed that these pacemaker aggregates produced by genetic manipulation be referred to as "induced sinoatrial bodies" (iSABs). Furthermore, the iSABs produced are functional in terms of their potency to stably stimulate the ventricular myocardium ex vivo. In addition, the RNA-seq-assisted analyses provided the first global mRNA expression patterns of pacemaker cells derived from stem cells as a basis for study of novel factor and/or marker combinations as tools for the programming and purification of pacemaker cells.

It is remarkable that the initial pilot experiment with solely TBX3-based programming led to doubling of the number of functional pacemaker cells in the aggregates were significantly lower beat frequencies. However, the enrichment was drastically increased further by the introduction of the additional Myh6-promoter assisted step of antibiotic selection. The basic idea was based on a recent publication which describes the enrichment of ventricular and noble cardiomyocytes via a Myh6-assisted selection [15] [17] [18], even though this method was originally intended for the open-ended enrichment of cardiomyocyte subtypes.

On the other hand, the fact that TBX3 alone does not lead to pure populations of ESC-derived node cells, is in accordance with its inability to accomplish complete direct reprogramming of the ventricular myocardium to form pacemaker cells [4]. Recently, it has been enthusiastically reported that Tbx18, a further T-box transcription factor, enables the direct conversion of the working myocardium to sinoatrial node cells ("iSAN"). While Tbx18 does appear more promising than Tbx3 in this specific connection, there exist concerns, for example the very low efficacy and relatively slow beat frequencies. Furthermore, this viral approach will be controllable only with great difficulty in vivo [5]. The new paper [5a] from this group shows exactly that: the viral vector was also found in the lung and spleen, and even in the heart there was no clearly focused area. In addition, in a large-animal model in vivo, it was possible to maintain the pacemaker cell function only for two weeks and then it was lost again. Moreover, it is unclear to date whether the adenoviral infection in the heart could lead to inflammation and/or arrhythmia.

The inventive approach likewise differs from previous publications that simulate biological pacemakers solely through the manipulation of terminal effector molecules that form the basis of sarcolemmal electrophysiology, rather than producing fully functional node cells de novo [29] [30]. By contrast, the protocol of the invention leads to cells which do not just have electrical oscillations but also the subtle electrophysiological and $Ca^{2+}$ signal properties and marked morphological features of native pacemaker cells. Therefore, the method of the invention represents a basis for future alternatives to electronic pacemakers.

Even though the pacemaker cells produced here form a synchronized and rapidly beating syncytium and are capable of forming electrical connections with ventricular slice cultures ex vivo and of stimulating contractions therein, it is still necessary, however, to analyze the potential thereof to become intracardially anchored and stimulate contractions with physiological beat rates. Applicability of the protocol to human pluripotent stem cells (i.e. hESCs, hiPSCs) [31] [32] [33] [34] [35] [36] is directly possible. This may ultimately smooth the way to applicability of cell-based biological pacemakers, which is of great significance for clinical applications and for medicament screening in vitro.

Materials and Methods q RT-PCR

Quantitative real-time PCR was conducted using RNA isolated with the Rneasy kit (Qiagen). The first-strand cDNA was conducted from 2 μg of RNA with AMV reverse transcriptase (Amersham) and random hexamer primer at 37° C. The real-time PCR was conducted with an iCycler and the MyiQDetection system (Biorad) using the IQ Syber Green Super Mix Kit (Biorad). The primer was constructed with the DNA-Star software and the specificity of each primer pair was confirmed by means of agarose gel electrophoresis. The annealing temperature was 57° C. for all primer pairs and the amplified murine cDNA fragments correspond to by 812-934 of the mGAPDH and by 287-429 of human TBX3 (hTbx3). All samples were analyzed as duplicates and the total RNA that was formed by combination of undifferentiated and differentiated ES cells and from murine hearts was used as control and to draw up a standard curve for the analyzed markers. The total RNA of each sample without reverse transcriptase was used as negative control. In the absence of the reverse transcriptase, no signal was obtained after 40 PCR cycles, which indicates that all samples were free of contaminating DNA. In addition, no signal was obtained either when reverse transcriptase was added without the RNA template, which indicates that there was no contamination by exogenous RNA or DNA. The standard curve for all genes showed an increase from a threshold cycle for each halving of the template concentration. The evaluation of the relative gene expression intensity was conducted on the basis of the ACT method. Factors of changes in the relative intensity of mRNA expression were calculated using GAPDH as reference gene, defining the expression value in the control cells as 1.

Patch-Clamp Technique

Spontaneous action potentials and currents of contracting cardiomyocytes were recorded at 37° C. in the perforated patch configuration using a MultiClamp 700B amplifier and pClamp10 software (Molecular Devices, Union City, USA). The offline data analysis was conducted with Clampfit software (Molecular Devices, Union City, USA) or by means of Origin 6.0 software (Microcal, Northampton, USA). Patch pipettes were drawn from borosilicate glass and heat-polished, and had a resistance of 2-5 MΩ on filling with intracellular solution which contained 10 mM NaCl, 130 mM potassium aspartate, 0.04 mM $CaCl_2$, 3 mM Mg-ATP, 10 mM HEPES and 200 μg/ml amphotericin B, pH adjusted to 7.2 with KOH. The extracellular (bath) solution contained: 140 mM NaCl, 5.4 mM KCl, 1 mM $MgCl_2$, 1.8 mM $CaCl_2$, 5 mM HEPES, 5.5 mM glucose; the pH was adjusted to 7.4 with NaOH. For better recording of the $I_f$, in some cases, 2 mM $BaCl_2$ and 0.3 mM $CdCl_2$ were added to the bath solution in order to block $I_{K1}$ and $I_{Ca}$. $I_f$ was measured by stepwise change proceeding from a hold potential of −40 mV to test potentials between −130 mV and +20 mV. The current amplitude after 3 seconds during the −130 mV pulse was divided by the cell capacitance in order to determine the current ($I_f$) density. To determine the $I_f$ activation kinetics, the time constant of the activation (τ) was obtained by fitting the current trace of the −130 mV step after the initial delay with the sum of two exponential functions $y=A_1 e_1^{-x/\tau)}+A_2 e_2^{(-x/\tau)}$, where $\tau_1$ and $\tau_2$ are fast and slow time constants for the activation; $\tau_1$ is accordingly referred to as τ, since the slow component ($A_2$) of the HCN channel activation is generally <10% of the current amplitude. Isoproterenol or carbachol (Sigma, Taufkirchen, Germany) was dissolved directly in the bath solution on the day of the experiment and the cells were administered by means of a rapid exchange superfusion system. APs were recorded with a 10 kHz sampling rate. The analyses were conducted on the original traces. The inclination/slope of the linear fit of the distance from the MDP to the potential threshold is the DDR; the AP duration is the time from the threshold potential to the MDP.

$Ca^{2+}$ Imaging

All $Ca^{2+}$ transients were measured by means of fluorescence imaging microscopy (Visitron Systems) and analyzed with VisiVIEW® imaging software. The $Ca^{2+}$ signals were recorded at an emission wavelength of 525/50 nm with an excitation wavelength of 470/40 nm (50 ms) using a cooled CCD digital camera in a 4*4 binning mode. The iSABs and aCaBs were loaded with 2.5 µM Fluo-4/AM in differentiation medium at 37° C. for 30 min. After second change of medium, the measurements were conducted at a temperature of 28° C. The $Ca^{2+}$ transients in ESCs as the peak value of the fluorescence intensity (F) are normalized to the minimum fluorescence intensity (Fo) during the time analyzed.

Spontaneous $Ca^{2+}$ transients were affected by the inhibition of the HCN channels with 5 µM ZD 7288 (Sigma-Aldrich), the inhibition of the voltage-dependent T-type $Ca^{2+}$ channels with 1 µM mibefradil (Sigma-Aldrich) and the inhibition of the voltage-dependent L-type $Ca^{2+}$ channels with 1 µM nifedipine (Sigma-Aldrich). For the experiments relating to blocking of the sarcolemmal $Ca^{2+}$ transport, the culture medium was replaced by a Tyrode's solution in a composition of (in mM): LiCl 140, KCl 6, MgCl 1, glucose 10, EGTA 1, HEPES 5, pH 7.4 (adjusted with KOH). The influence of the $Ca^{2+}$ stores on the $Ca^{2+}$ transients was examined by the addition of caffeine (10 mM, Sigma-Aldrich), in order to open the ryanodine coupled SR-$Ca^{2+}$ channels, and of thapsigargin (2 µM, Sigma-Aldrich), in order to inhibit the SERCA. ZD 7288, nifedipine and Fluo-4/AM were dissolved in DMSO (final concentration <0.1%), and thapsigargin in ethanol (final concentration 0.2%). Mibefradil and caffeine were dissolved in $H_2O$.

Slice Preparation and Culture

The experimental protocols for the animal experiments were approved by the competent Bavarian government authority and conducted in accordance with the *Guide for the Care and Use of Laboratory Animals* (National Institutes of Health, publication no. 85-23, revised 1996). Hearts from adult mice of both genders were rapidly removed and transferred to an ice-cold modified Tyrode's solution (composition in mM): NaCl 136, KCl 5.4, $MgCl_2$ 1, $CaCl_2$ 0.9, $NaH_2PO_4$ 0.33, glucose 10, 2,3-butanedione monoxime 30, HEPES 5, pH 7.4 (adjusted with NaOH). The ventricles were freed of the arteries, flaps and vessels and embedded in a 4% low-melt agarose gel which was dissolved in the modified Tyrode's solution without glucose. The agarose containing the heart was stuck to the sample vessel of the Vibratom (VT1200S, Leica) and covered quickly with ice-cold Tyrode's solution. The hearts were sliced parallel to the plane of the flaps into 300 µm-thick tissue slices with steel blades (Wilkinson), which gave annular slices of the ventricular myocardium.

At incubation for 30 min in ice-cold Tyrode's solution, the slices were applied to a Biopore™ membrane of tissue culture inserts (Millicell, Millipore) for cultivation at an air/medium interface. The tissue culture inserts were placed into petri dishes that contained culture medium M199, enriched with 1% insulin-transferrin-selenium (Gibco) and 1% penicillin/streptomycin (Sigma). The slices were cultivated in an incubator (37° C., 5% $CO_2$) until the co-culturing stage. For routine determination of the viability of the slices, they were incubated with thiazolyl blue-tetrazolium bromide (MTT, 0.5 mg/mL, Sigma) at 37° C. for 40 min and analyzed under a light microscope.

Co-Culture of iSABs with Heart Slices iSABs was labeled with CalceinRed™ (AAT Bioquest) to observe the living cells. For this purpose, iSABs were incubated in the incubator with 10 mg/ml CalceinRed™/AM in differentiation medium at 37° C. for 30 min. After centrifugation (1000 rpm, 5 min) and resuspension in differentiation medium, the iSABs were applied with a pipette under the microscope to the murine heart slices. iSABs and heart slices were co-cultivated in the incubator (37° C., 5% $CO_2$). The beat frequencies of the iSABs and the slice regions were recorded daily using a Sony NEX-5N camera. The coupling between iSABs and the slices by the transfer of CalceinRed™ from the iSABs into the cells of the sections was detected by means of fluorescence imaging (Ex/Em 646/659 nm, Visitron Systems). The contact regions of the iSABs with the slices were recorded daily and the distribution of the CalceinRed™ fluorescence was analyzed visually.

$Ca^{2+}$ Imaging in Contact Regions of the iSABs with the Slices

The slices with iSABs were laden with 5 µM Fluo-4/AM (Invitrogen) in M199, enriched with 1% insulin transferrin selenium (Gibco) and 1% penicillin/streptomycin (Sigma) at 37° C. for 30 min. The $Ca^{2+}$ signals were recorded by fluorescence imaging microscopy (Visitron Systems) at an emission wavelength of 525/50 nm and with an excitation wavelength of 470/40 nm (exposure time 30 ms) using a cooled CCD digital camera in a 4*4 binning mode. All $Ca^{2+}$ transients were analyzed with VisiVIEW® imaging software and the peak value reported was the fluorescence intensity (F), normalized to the minimum fluorescence intensity (Fo) during the analysis time (20 s) in the corresponding regions.

Cell Culture

The ES cell lines derived from the murine cell line GSES [37] were grown in DMEM medium with highly concentrated glucose and stable glutamine (GIBCO), containing 10% FBS Superior (Biochrom), 100 µM non-essential amino acids (GIBCO), 1% penicillin/streptomycin (GIBCO) and 100 µM β-mercaptoethanol (Sigma), in the presence of 1000 U/mL leukemia-inhibitory factor (LIF, Milllipore). Differentiation was conducted according to standard protocols in Iscove's basal medium (Biochrom) containing 10% FBS (Biochrom), 100 µM non-essential amino acids (GIBCO), 1% penicillin/streptomycin (GIBCO) and 450 µM 1-thioglycerol [13]. The passage of the cells was conducted with trypsin/EDTA (GIBCO) at 70% confluence, which was normally attained after 2 to 3 days. The differentiation was usually conducted 3 to 4 passages after thawing of the cells. The cells were transformed with 15 μg of plasmid DNA using JetPEI (Peqlab) and subsequent selection with 10 μg/mL blasticidin (Invivogen) or 250 μg/mL hygromycin (Invitrogen) in 10 cm tissue culture dishes. Stable clones were selected manually, then cultivated and tested by means of qRT-PCR and differentiation assays [13]. For induction of the spontaneous formation of aCaBs and iSABs, positive clones, as recently described [15], were treated with antibiotics for enrichment of cardiomyocytes. The single cells required for the physiological analyses which follow were isolated enzymatically as described [14][16]. To ensure the successful production of aCaBs and iSABs, possible contaminations with mycoplasms were monitored regularly twice per week with the PCR-based MycoSPY kit system (Biontex).

RNA Sequencing

For the production of a library and for sequencing, the culture medium of the cultivated adherently growing cells was decanted, and the cells were washed and lyzed directly by addition of lysis buffer. Of this lyzate, 1 μL was used for the cDNA synthesis and amplification with the SMARTer kit (Clontech, Mountain View Calif., USA) in accordance with the manufacturer's instructions. The cDNA synthesis was started by annealing a polyA-specific primer and adding a reverse transcriptase with terminal transferase activity. Subsequently, the newly synthesized first-strand cDNA was first extended with a homopolymer stretch by the terminal transferase and then with a specific application tag by means of template switching. The resulting double-labeled cDNA was amplified by means of PCR, fragmented by ultrasound treatment (Bioruptor, Diagenode, Liege, Belgium; 25 cycles with 30 s on/30 s of) and converted to bar-coded Illumina sequence libraries using the NEBnext Ultra DNA library preparation kit (New England Biolabs, Ipswich Mass., USA). After PCR enrichment, the cDNA libraries were purified with AmpureXP magnetic beads (Beckman-Coulter, Brea Calif., USA) and quantified in a Bioanalyzer 2100 (Agilent, Santa Clara Calif., USA). The cDNA libraries were combined with equimolar amounts and sequenced in a IlluminaGenomeAnalyzerIIx in single-read mode with a read length of 78 nucleotides and a range from 21 million to 32 million raw reads per replicate.

For the subsequent mapping and the expression analyses, the reads from the Illumina sequencing were de-multiplexed and mapped with the mm9 mouse genome with the TOPHAT sliced-read (v1.4) [38] and a genome annotation (from iGenomes, http://cufflinks.cbcb.umd.edu/igenomes.html) for the assistance of the detection of the exon-exon boundaries. The assignment of the reads for each gene was obtained with HTSeq (http://www-huber.embl.de/users/anders/HTSeq/) and normalized with the DESeq R package [39]. The differential expression was examined by means of DESeq with pair-by-pair comparison of each group with three biological replicates and with a false discovery rate set to 0.05. All sequence and data analysis steps were conducted on a local server of the Galaxy platform [40].

Ontology descriptions that are familiar to the person skilled in the art only in the English language have been left here in English.

(A) 82 gene ontologies which describe biological processes comprise 220 upregulated genes in iSABs vs. controls. (B) Cluster of ontology groups relating to heart/muscle function and heart development are dominant. (C) Consolidated network of the gene ontologies which relate to biological processes. (D) 34 gene ontologies which describe the cellular components comprise the 220 upregulated genes in iSABs vs. controls. (E) of ontology groups relating to structures typical of contracting cells are dominant. (F) Consolidated network of the gene ontologies which relate to cellular components.

FIG. 6: Representative Action Potentials Obtained From Tbx3-Programmed Cells (A, B) Myocardial types with (A) ventricular-type and (B) atrial-type action potentials. (C, D) Pacemaker-type action potentials with (C) mature sinoatrial-type action potentials and (D) slightly immature pacemaker-type cells which are referred to as intermediate-type cells of the murine embryonic heart. Horizontal time axis: 100 ms.

Figure 1A:
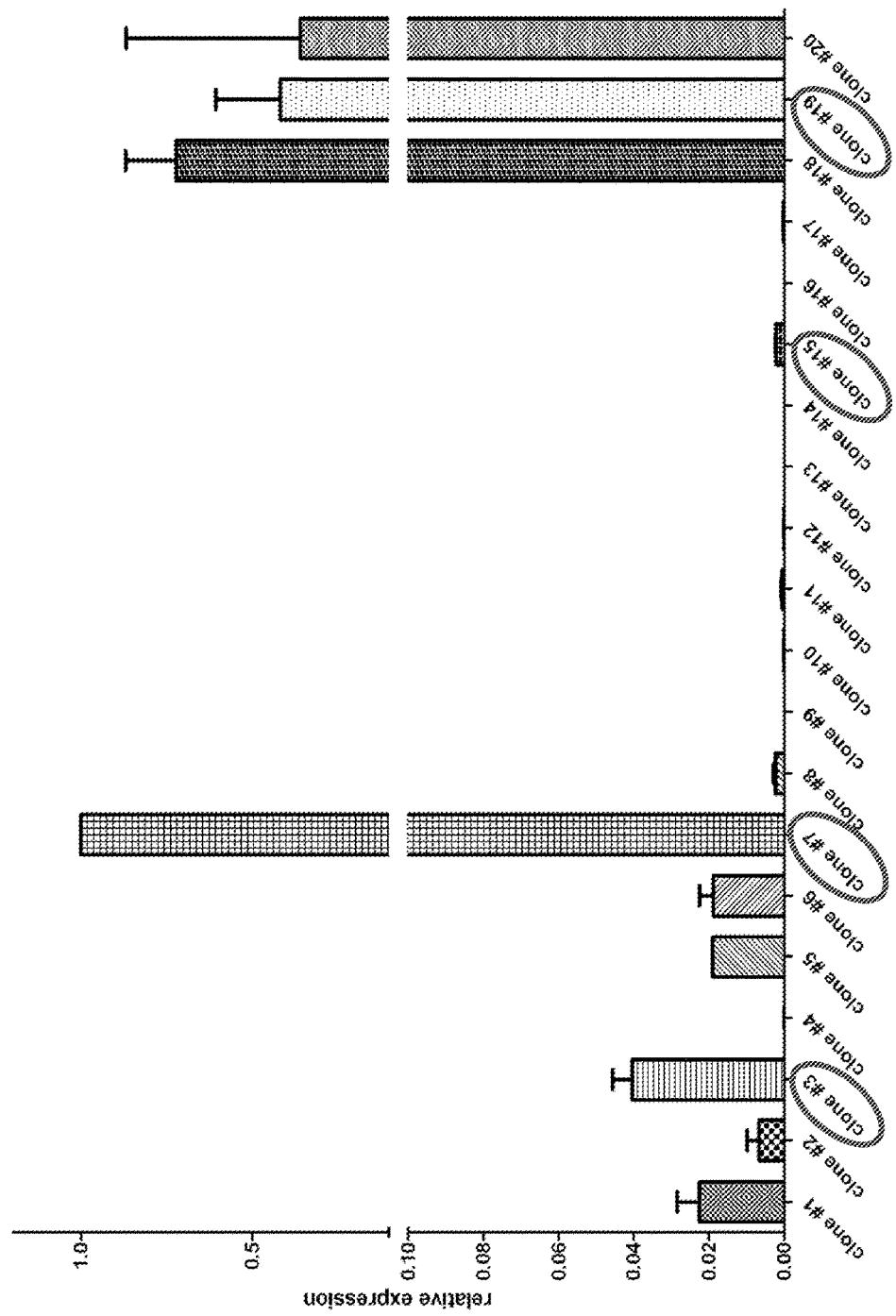
FIG. 1: Functionality of the TBX3 Overexpression Constructs in ES Cells (A) 20 independent cell clones stably transfected with the overexpression construct containing human TBX3 cDNA. The overexpression levels were analyzed by means of qRT-PCR. For further analysis, four representative clones were selected (data are reported as mean values±SD; n=2). (B) The immune staining of overexpressed TBX3 and actin in the four selected clones confirms the overexpression level of TBX3. (C) FACS analyses of Oct-4/Pou5f1 and Sox2 did not show any influence of TBX3 overexpression on pluripotency with the addition of LIF (data are reported as mean values±SEM; n=5).
Figure 1C:
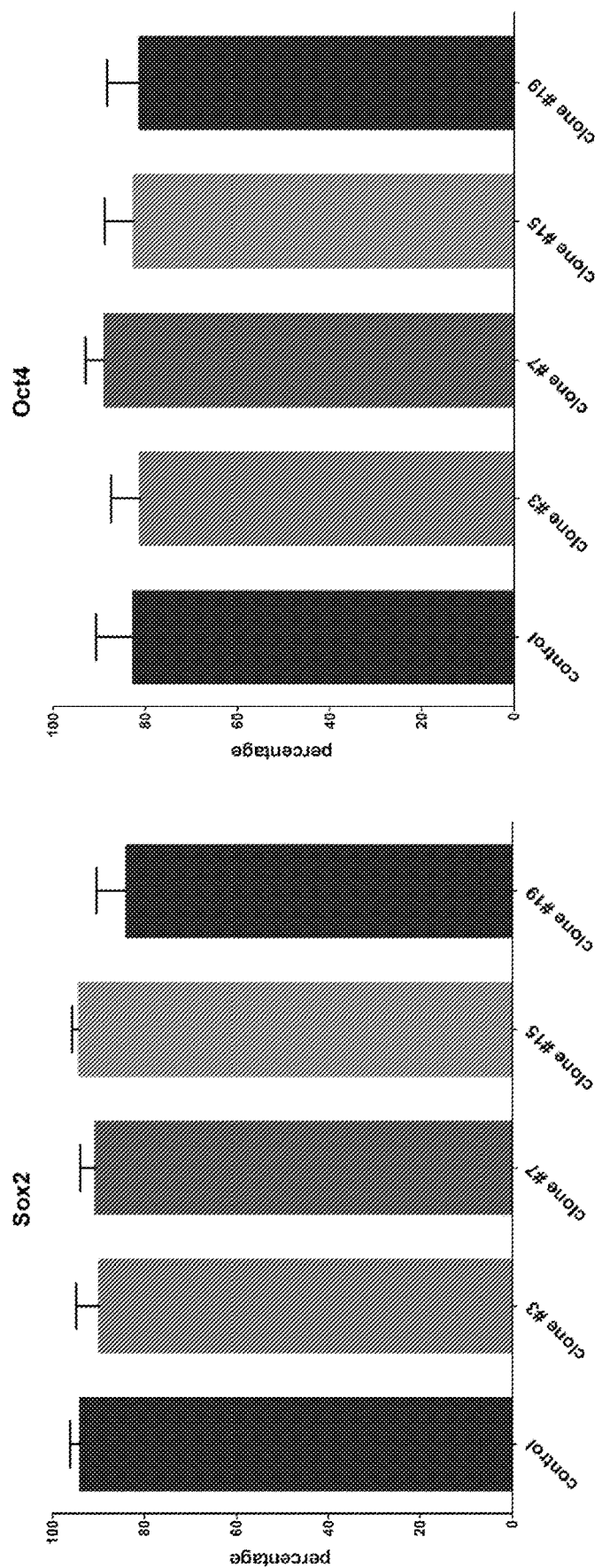
Figure 2B:
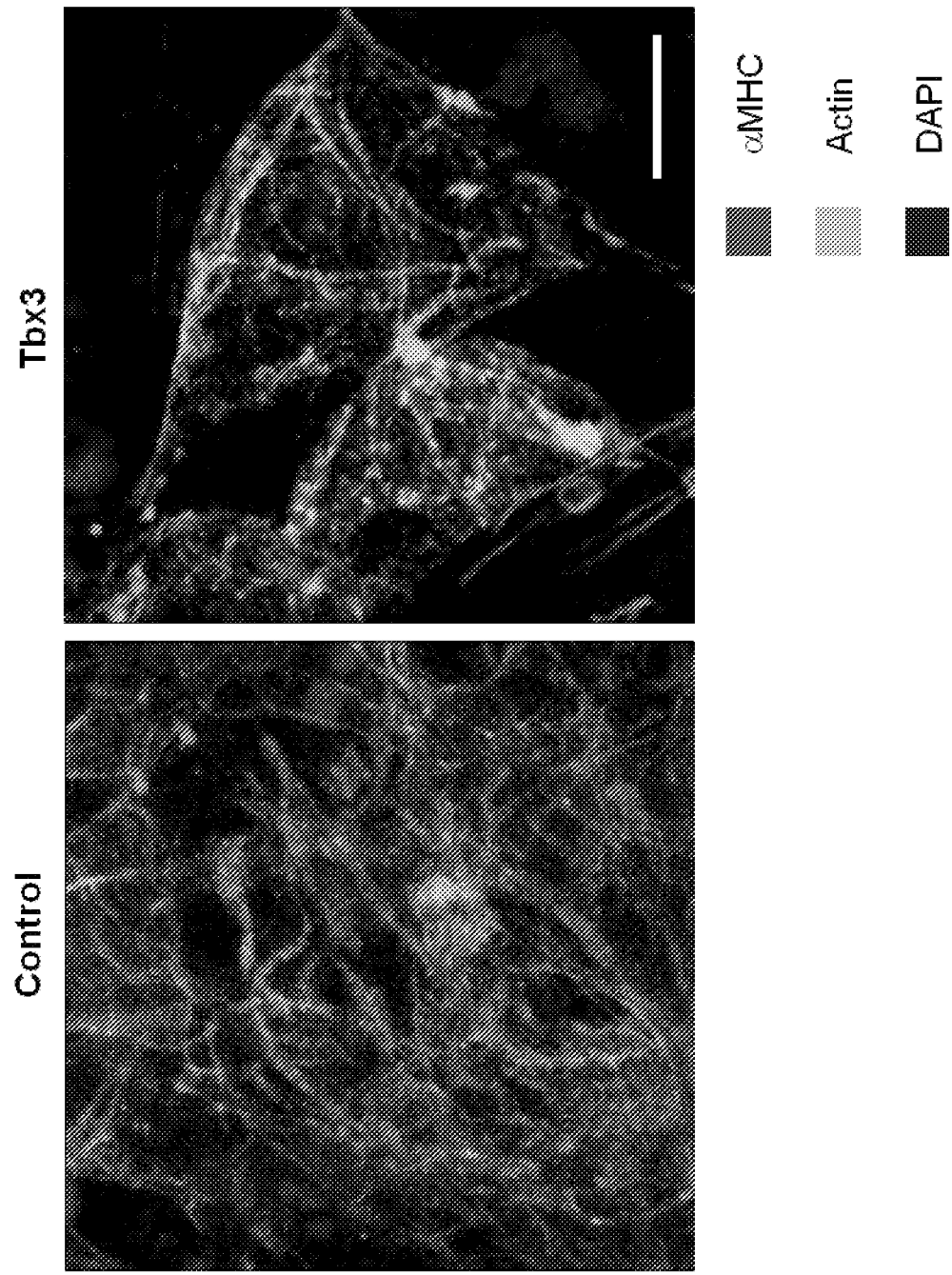
FIG. 2: Predominant Occurrence of Pacemaker-Type Cardiomyocytes in Tbx3-Differentiated ES Cells (A) Increase in spontaneous bead activity in independent TBX3 clones and in ES control cells (GSES) (data are reported as mean values±SEM, n>100). The control and the four clones clone #3, clone #7, clone #15 and clone #19 are each shown in this sequence from right to left, beginning in each case with the control shown in white. (B) Confocal analysis of Myh6 expression in control and TBX3-overexpressing cardiomyocytes. Counter-staining of actin and cell nuclei. Scale: 10 μm. (C) Distribution of the cardiomyocyte subtypes and Ventr.—ventricular (23.1%); Atr.—atrial (8%); Pace.—sinoatrial node-like (38.5%); Interm.—intermediate/early type (38.8%). Horizontal bar: 100 ms; vertical bar: 20 mV. (D) HCN4-expressing cells have significantly increased TBX3 clones on day 18 (data are reported as mean values±SD; n=5).
Figure 3A:
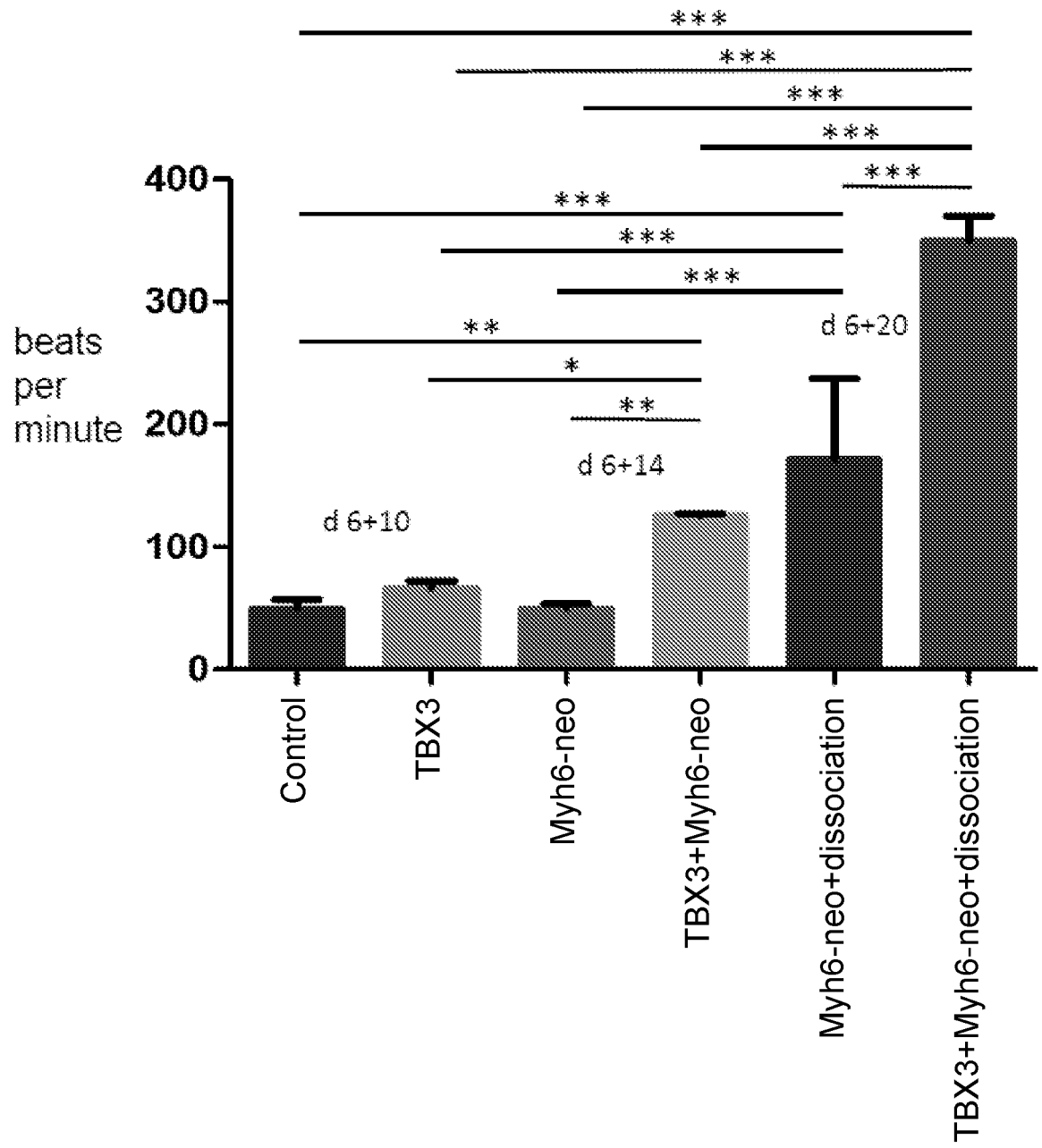
FIG. 3: Physiological Parameters of the Pacemaker-Type Cardiomyocytes Obtained by Combined Tbx3 Differentiation and Myh6 Promoter Selection (A) Beat frequencies against time after different treatment regimes of Myh6-neomycin controls and Myh6-TBX3 cells. The highest beat frequencies (300-400 bpm) are achieved by a combination of selective TBX3 programming, antibiotic selection and an additional dissociation step (data are reported as mean values±SD; 5). (B) Expression of HCN4 (left-hand region), Cx45 (middle region) and Cx30.2 (right-hand region) in iSABs. Counter-staining of actin and cell nuclei. Scale: 10 μm. (C) Typical elongated cell form of sinoatrial node cells in the synchronized cell layers obtained by plating out iSAB. Scale: 10 μm. (D) Distribution of the pacemaker cells as apparent from single-cell patch-clamp and funny channel measurement: more than 81% pacemaker-type cells were obtained. Of these, 19% were immature pacemaker cells, while the others were mature pacemaker cells; n=65, (E) Frequencies of spontaneous $Ca^{2+}$ transients in Myh6-TBX3 cells decrease significantly after inhibition of the HCN channels by ZD7288 (data are reported as mean values±SEM; n 7). (F) The frequencies of spontaneous $Ca^{2+}$ transients in Myh6-TBX3 cells decrease after inhibition of T-type and L-type $Ca^{2+}$ channels by mibefradil and nifedipine (data are reported as mean values±SEM; n>12). (G) Spontaneous $Ca^{2+}$ transients before and in the presence of 10 mM caffeine in cells derived from iSABs and aCaBs. The amplitude of the caffeine-induced peak in the former cells is comparable to the maximum of the spontaneous $Ca^{2+}$ transients. n 8. (H) Blockage of the $Ca^{2+}$ uptake into the SR by thapsigargin leads, by contrast to the cells derived from aCaBs, to increased diastolic $Ca^{2+}$ levels in the cells derived from iSABs. n≥11. (I) $Ca^{2+}$ transients before and after blockage of the $Na^+/Ca^{2+}$ exchanger and of the sarcolemmal $Ca^{2+}$ channels: in cells derived from iSABs, by contrast with the control cells derived from EBs, a large caffeine peak is observed. n>16. (J) $Ca^{2+}$ transients before and after inhibition of $Ca^{2+}$ uptake: inhibition of $Na^+/Ca^{2+}$ exchangers plus SERCA inhibition causes, by contrast with the cells derived from aCaBs, a rapid rise in intracellular $Ca^{2+}$ in cells derived from iSABs. n>24. In addition, in both cases, a small caffeine peak was observed. (K) The analysis of the SR $Ca^{2+}$ outflow, which is characteristic of cells active as pacemakers, shows an increased rate of accumulation of intracellular $Ca^{2+}$ in cells derived from iSABs compared to aCaBs. Blockage of the $Na^+/Ca^{2+}$ exchanger plus inhibition of SERCA brought about intracellular $Ca^{2+}$ accumulation comparable to the decrease in the caffeine peak in cells derived from iSABs. No difference in the rate of accumulation of systolic $Ca^{2+}$ and amplitude of the caffeine peak in cells derived from aCaBs. Mean value±SEM; #p<0.05 vs. no SERCA inhibition; *p<0.05 vs. control is.
Figure 3C:
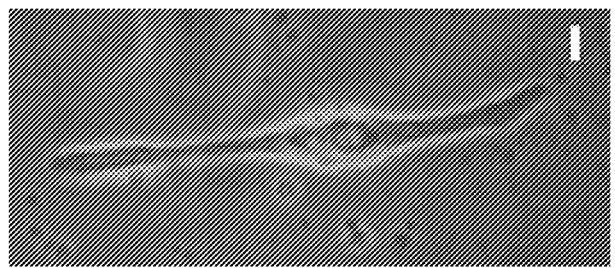
Figure 3D:
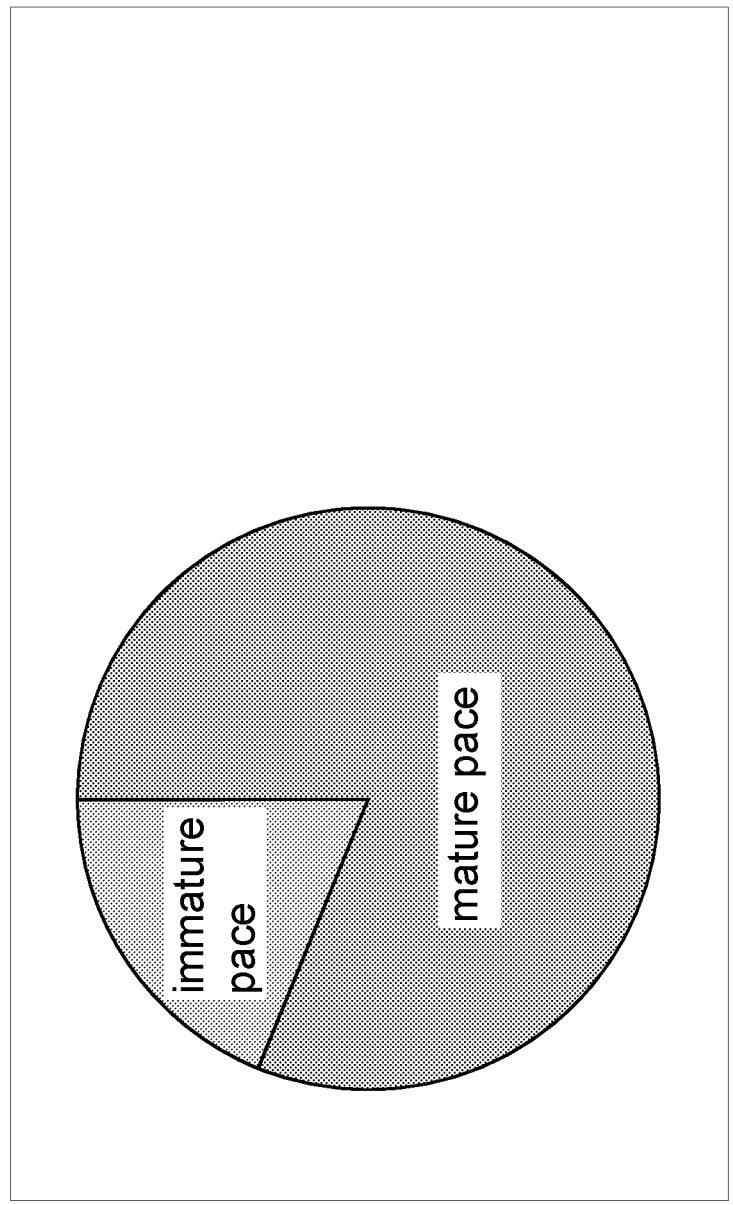
Figure 3E:
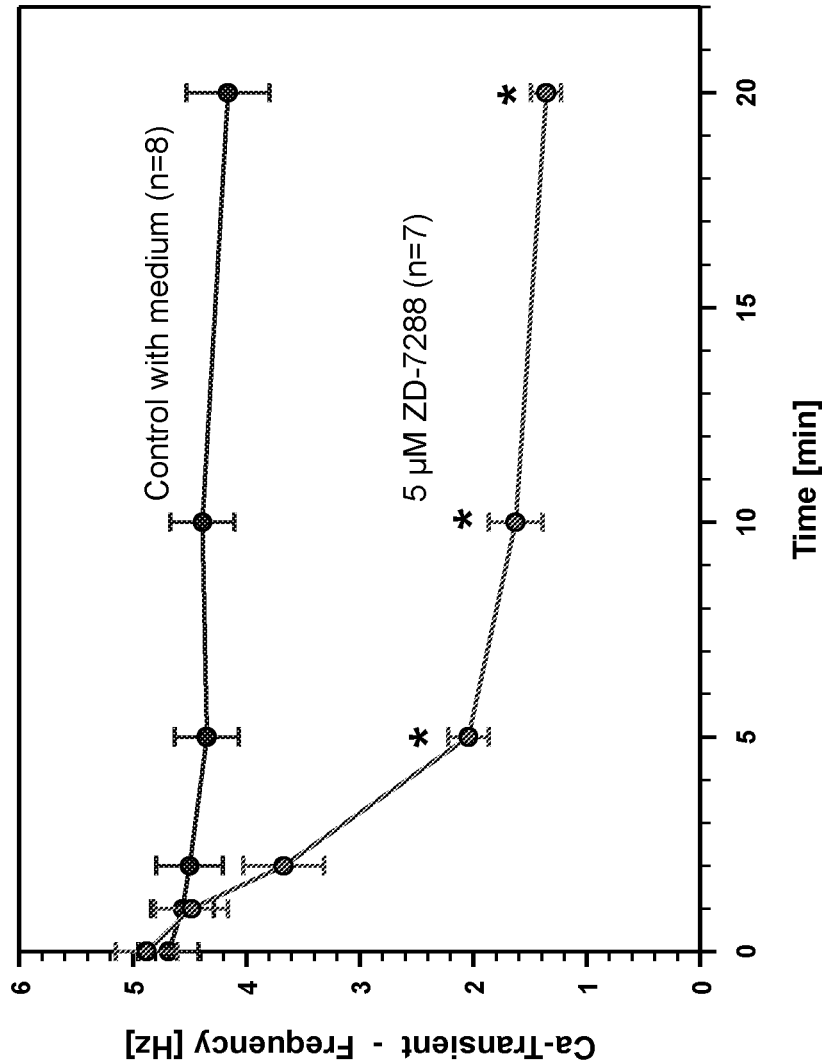
Figure 3F:
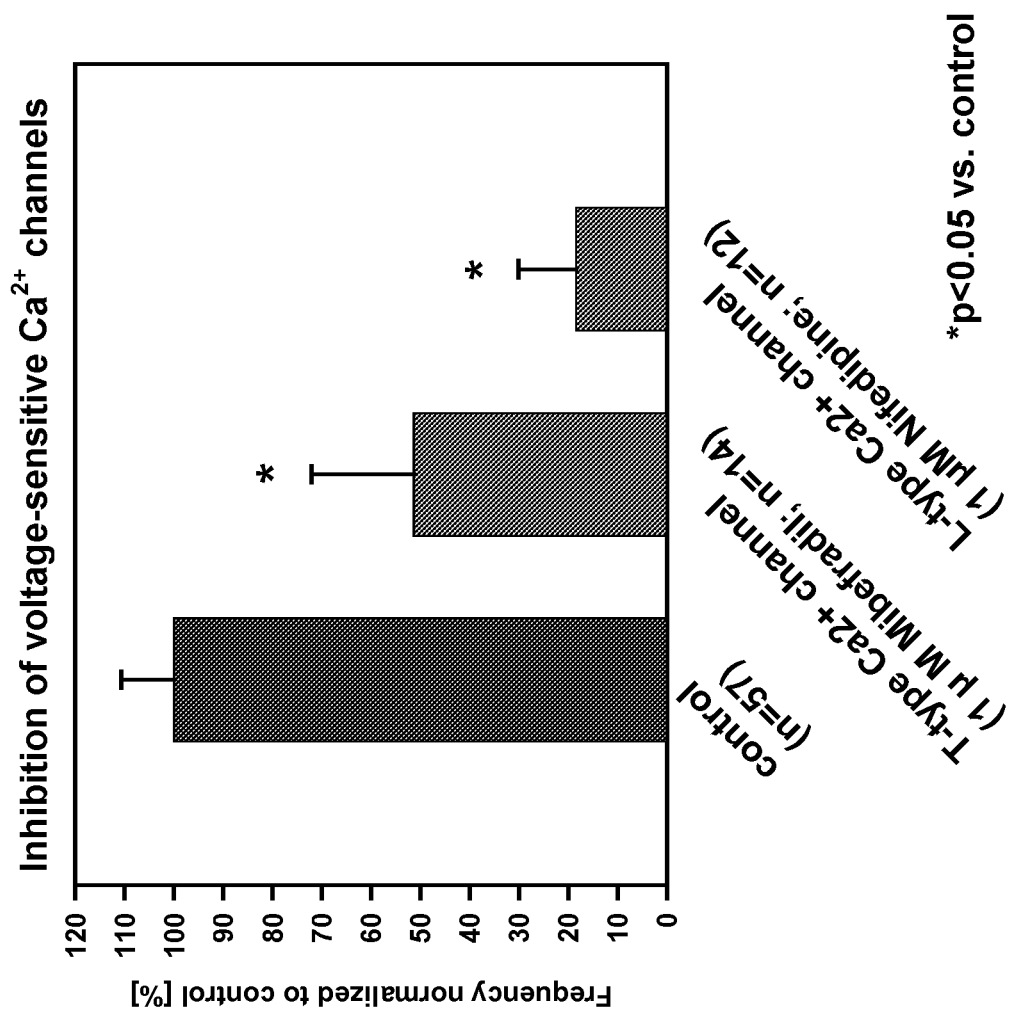
Figure 3G:
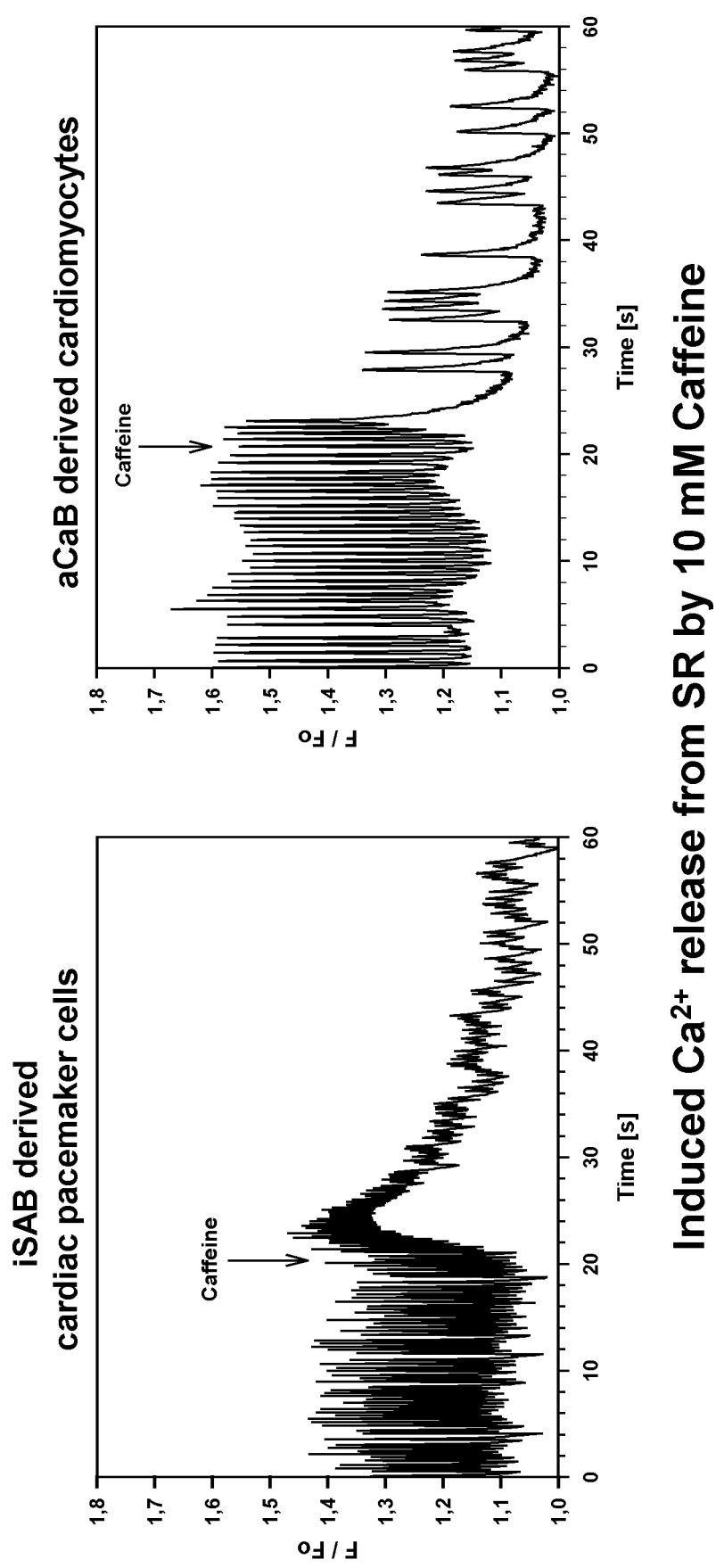
Figure 3H:
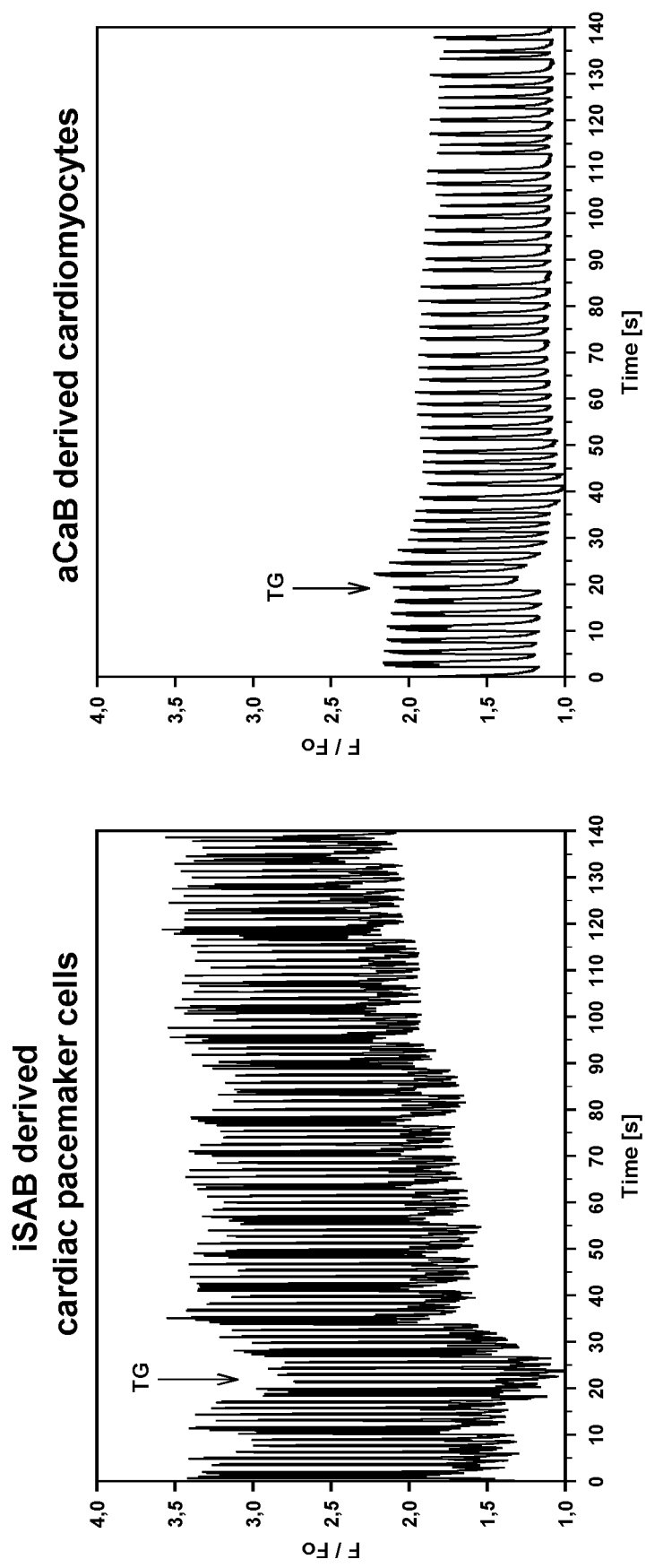
Figure 31:
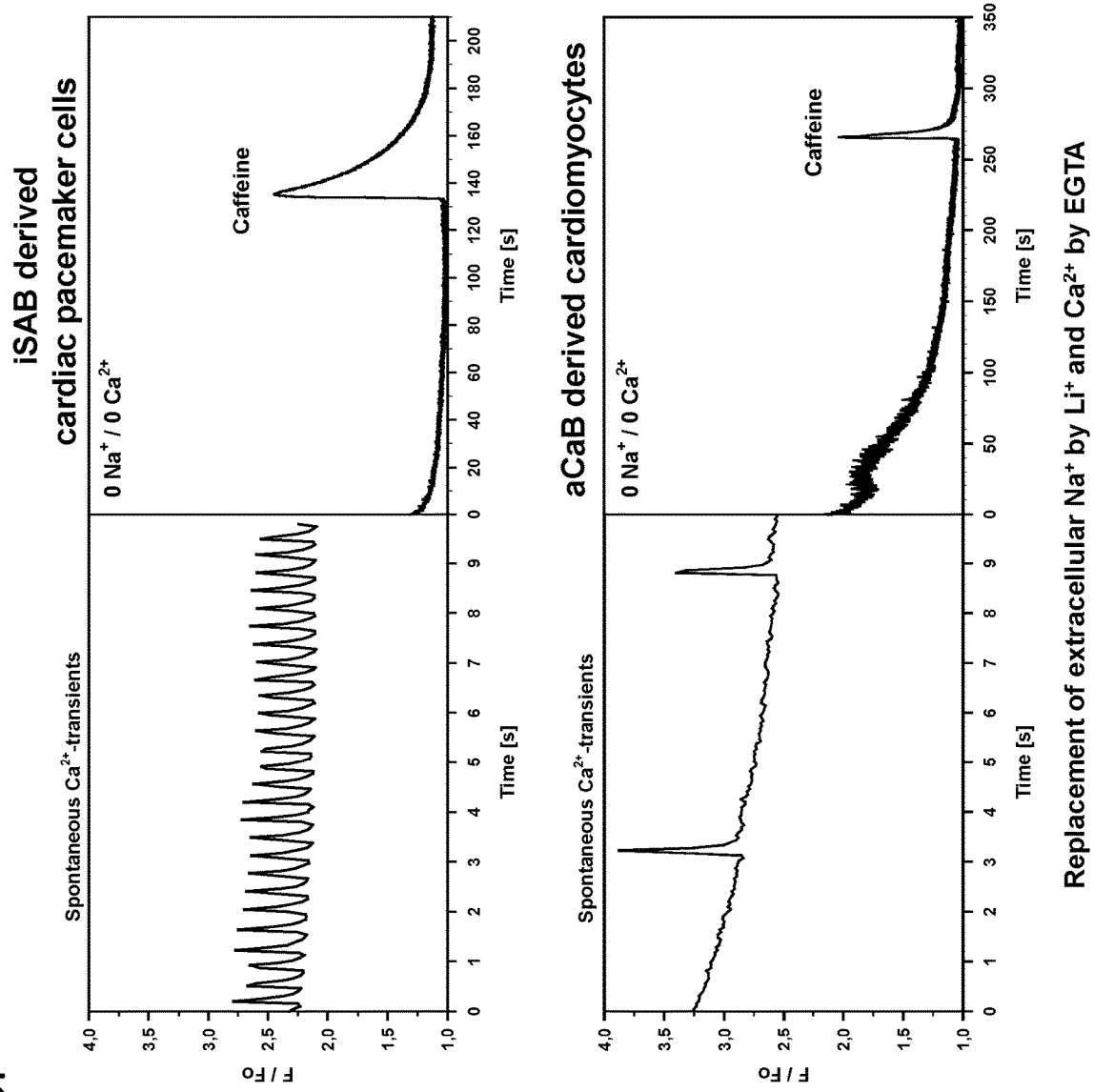
Figure 3J:
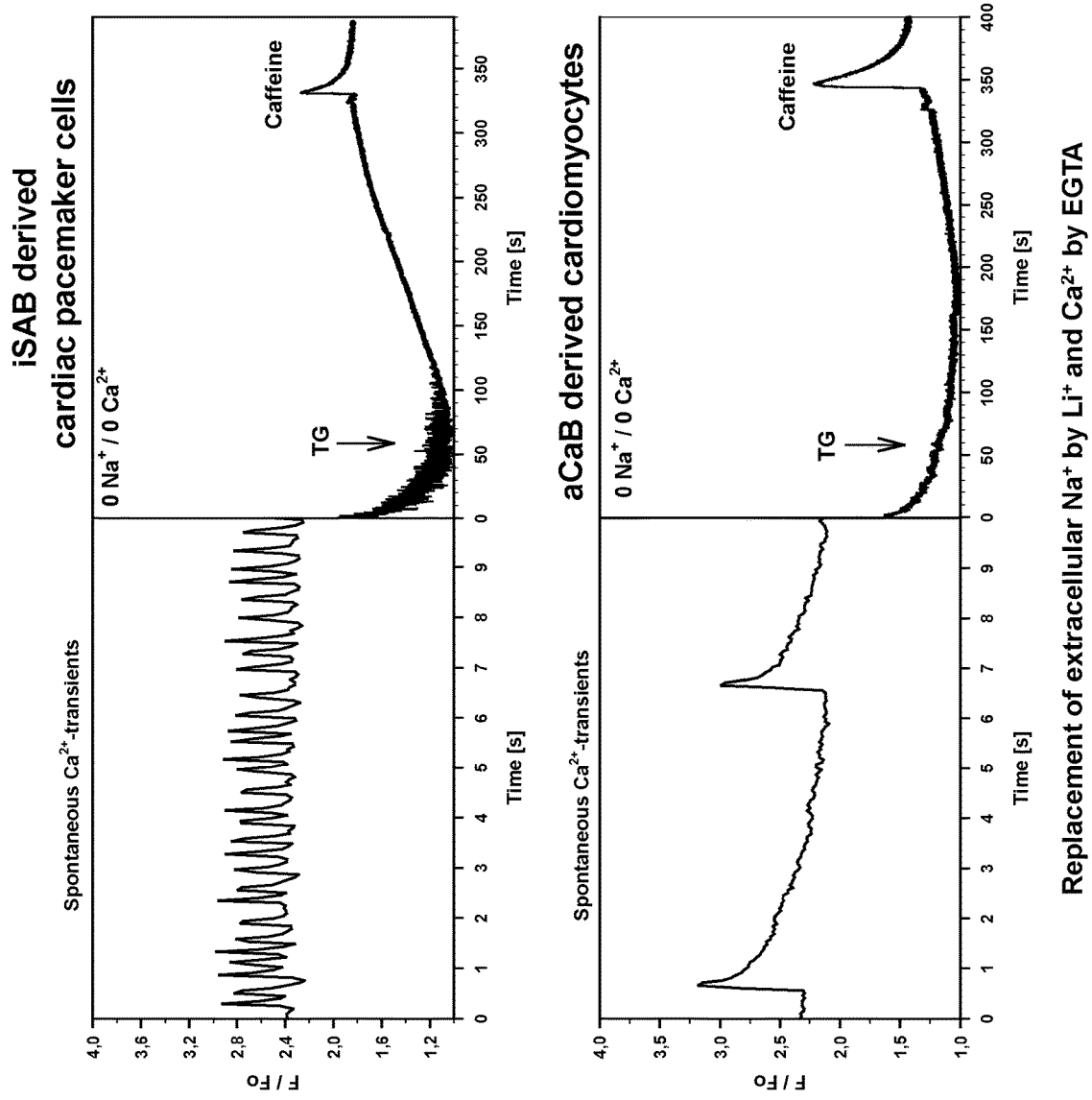
Figure 3K:
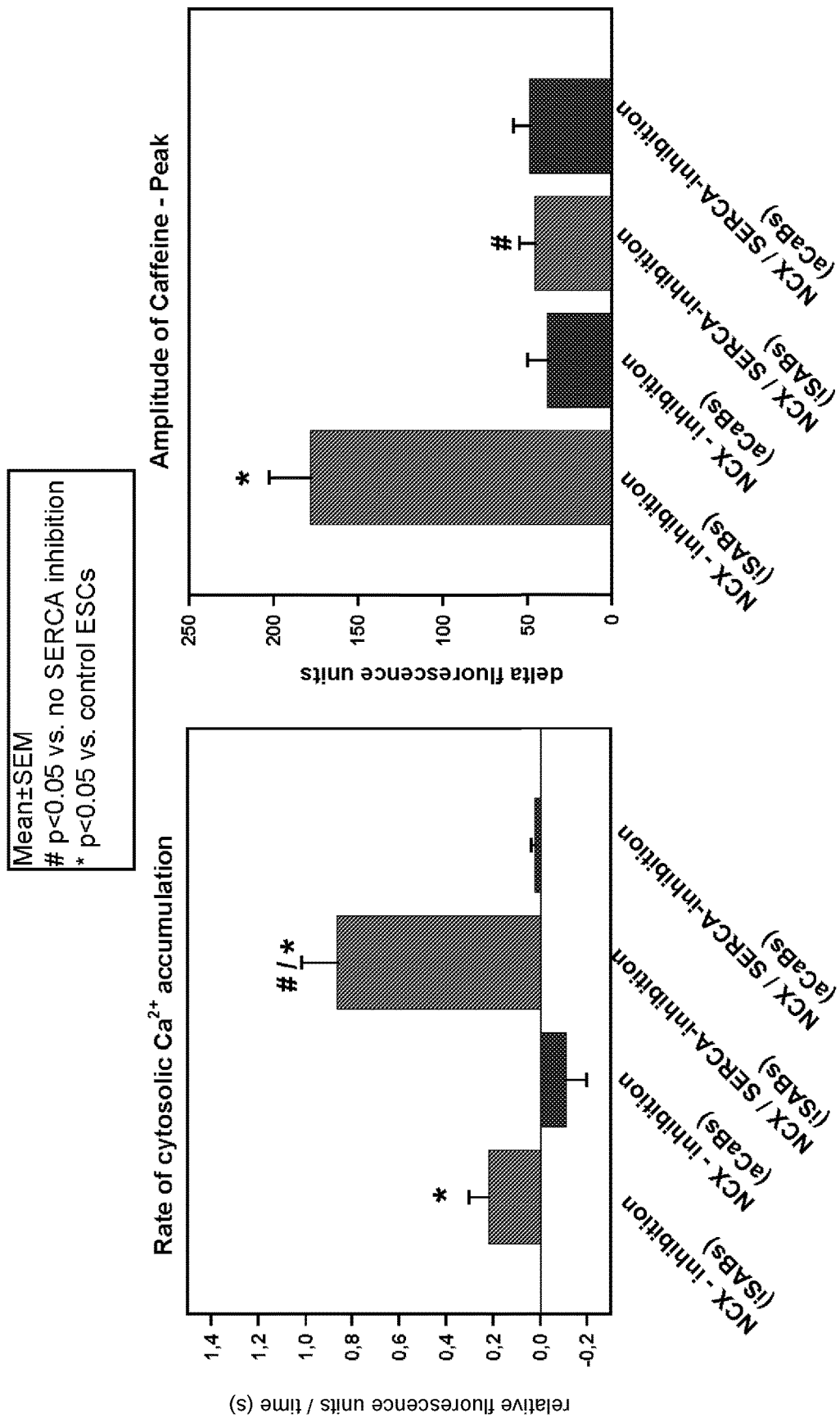
Figure 4C:
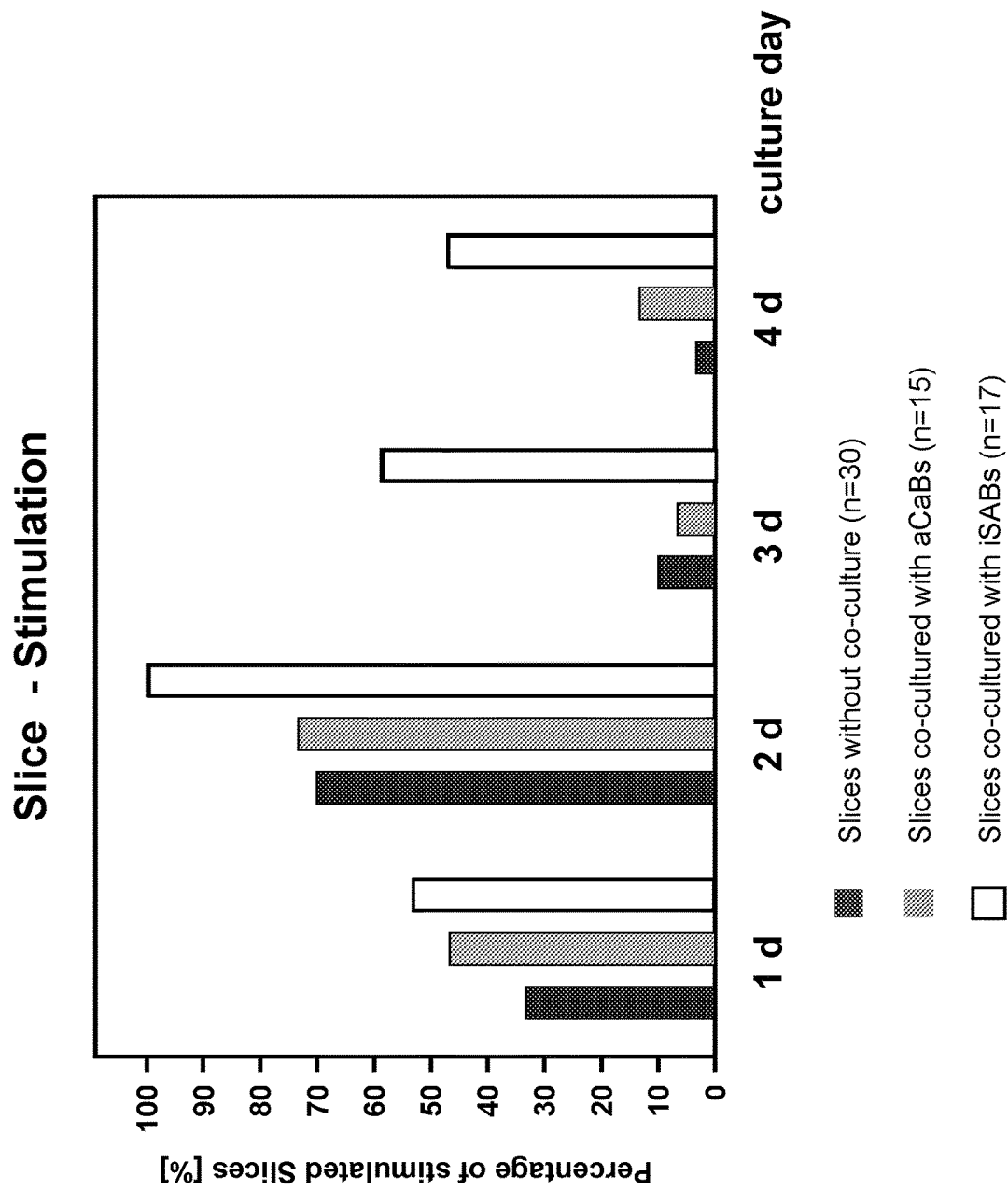
FIG. 4: Functionality of iSABs in the Ex-Vivo Model of Cultivated Murine Ventricle Slices (A) Ventricle slices cultivated for five days (left-hand region) and MTT stain for checking of vitality (right-hand region). (B) Identification of the DiI-labeled iSABs sown on a slice (right-hand region: overlay). (C) Percentage distribution of iSAB-sown, aCaB-sown and unsown slices containing at least one contracting region over time. The spontaneous activity decreases after day 2, while the activity in the slices sown with iSAB is maintained to a high degree (n≥15). (D) Average number of active regions per iSAB-sown, aCaB-sown and unsown slice over time (data are reported as mean values±SEM (MW SEM); n≥15). (E) Increase in the beat frequencies of slices sown with iSABs from day 1 to day 4 (data are reported as mean values±SEM ((MW SEM); n≥16). (F) Transfer of calcein dye from an iSAB to the recipient slice over time [scale: 200 µm; "h": hour(s); "d": day(s)]. (G) The stimulation of slice regions (arrows) in the immediate environment of an iSAB (arrow) is accompanied by highly synchronous $Ca^{2+}$ transients.
Figure 4D:
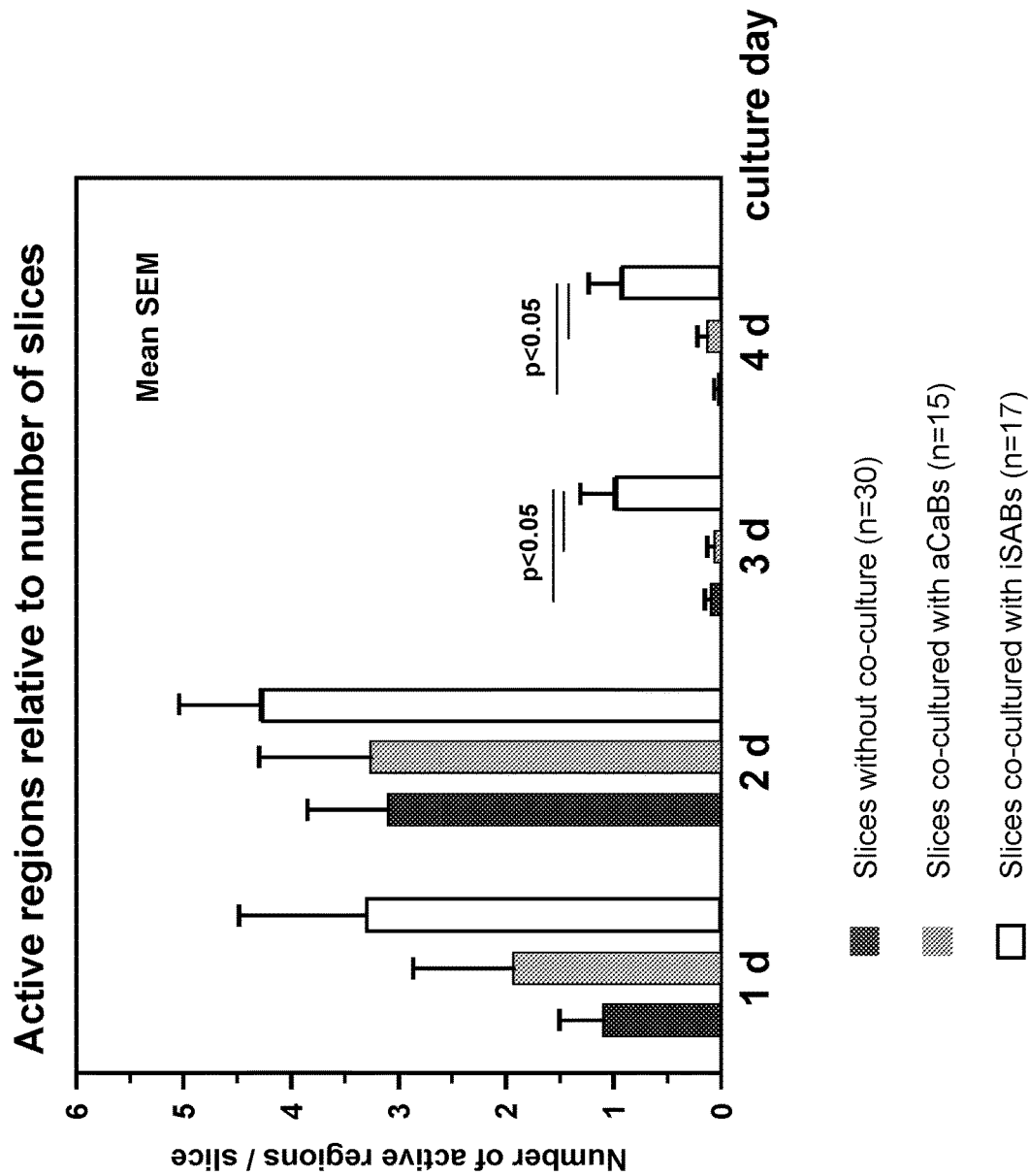
Figure 4E:
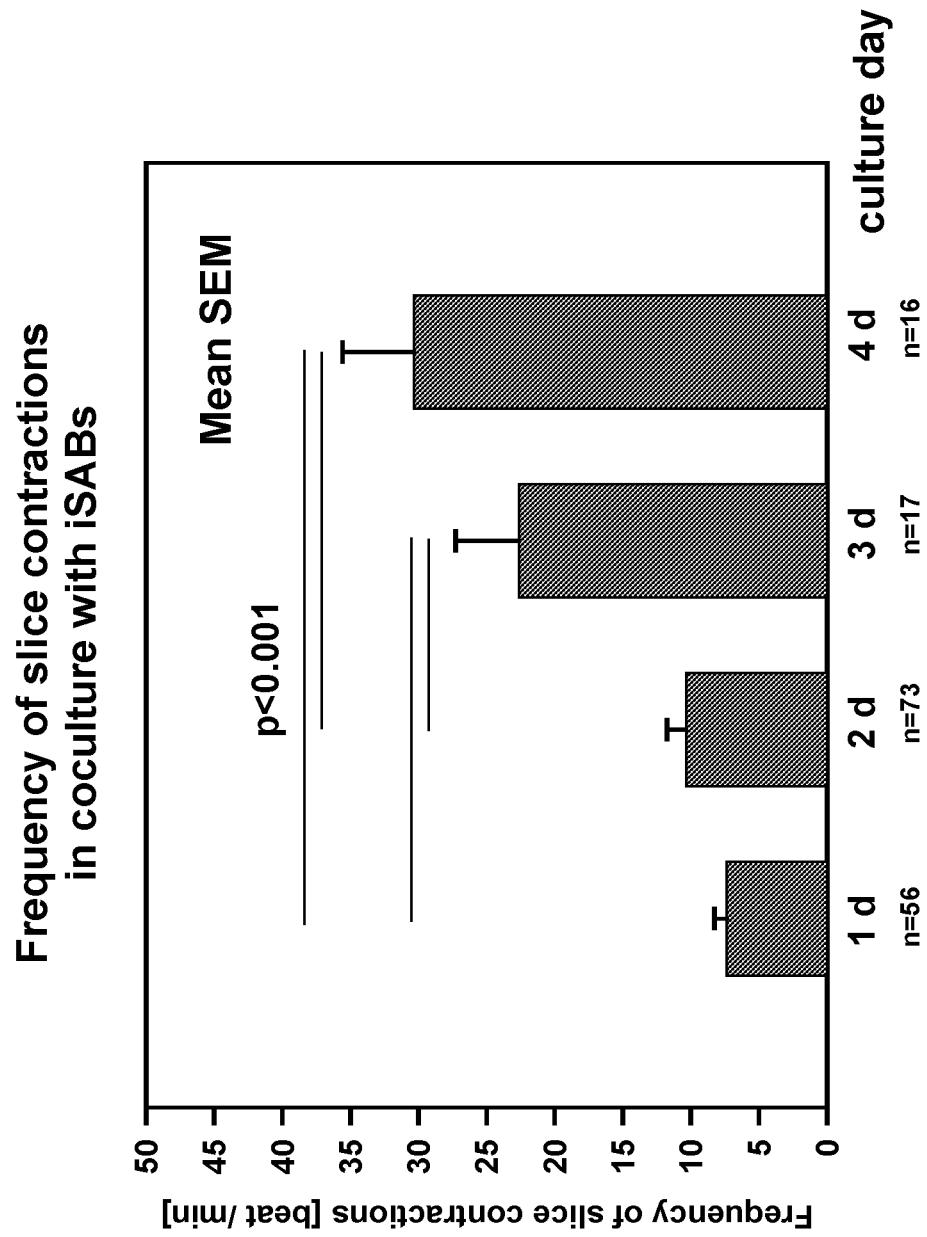
Figure 4F:
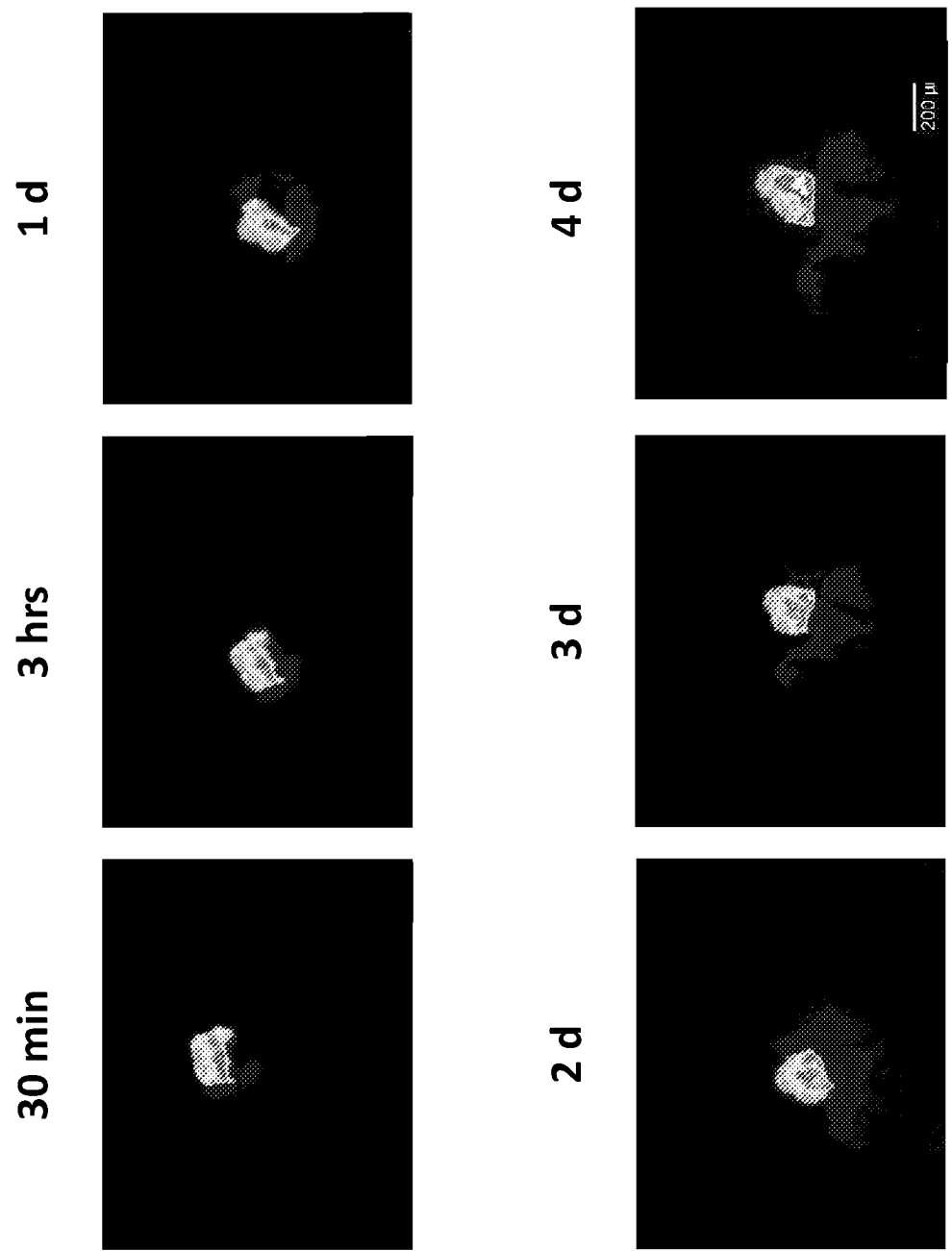
Figure 4G:
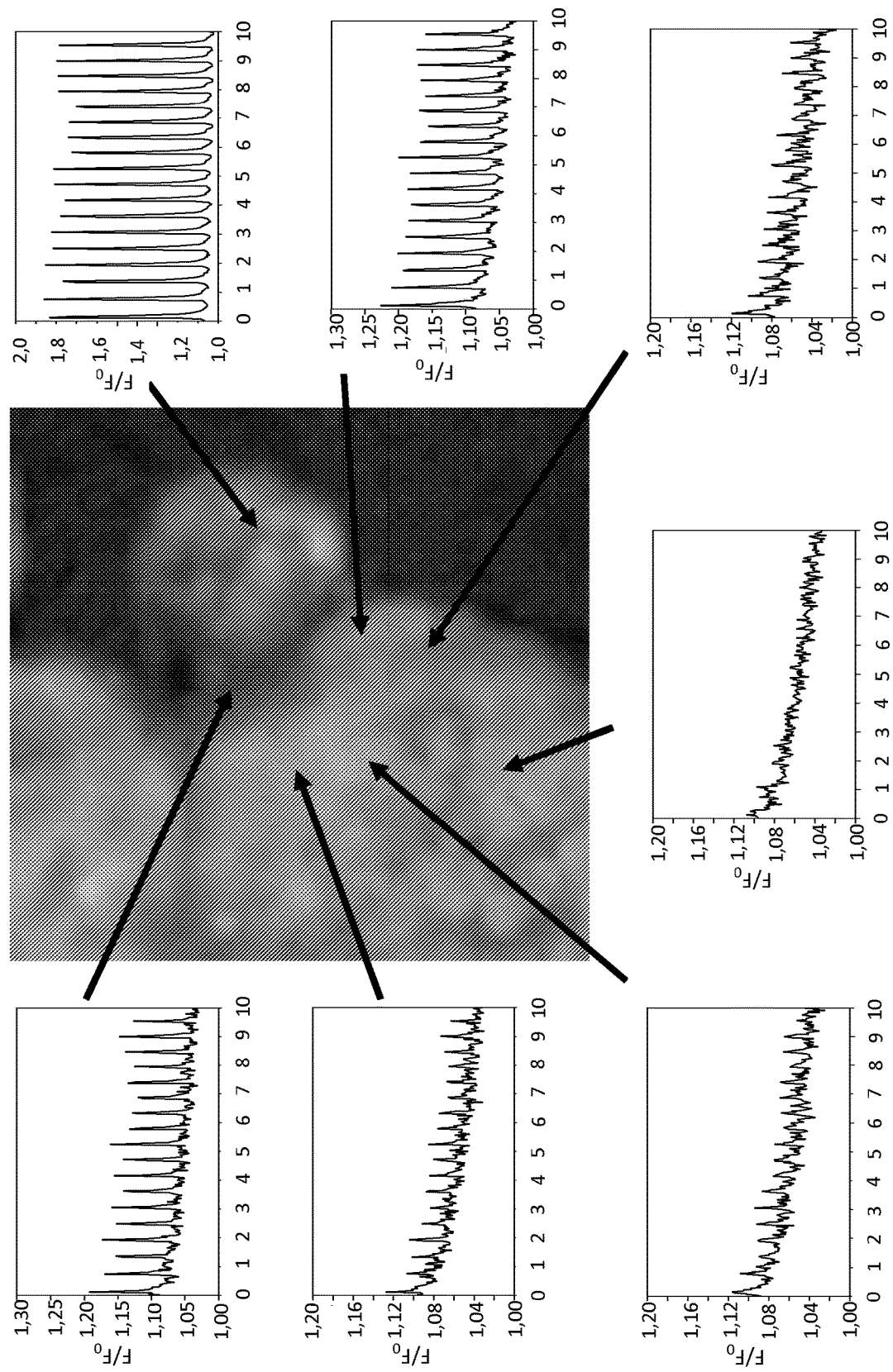
Figure 5A:
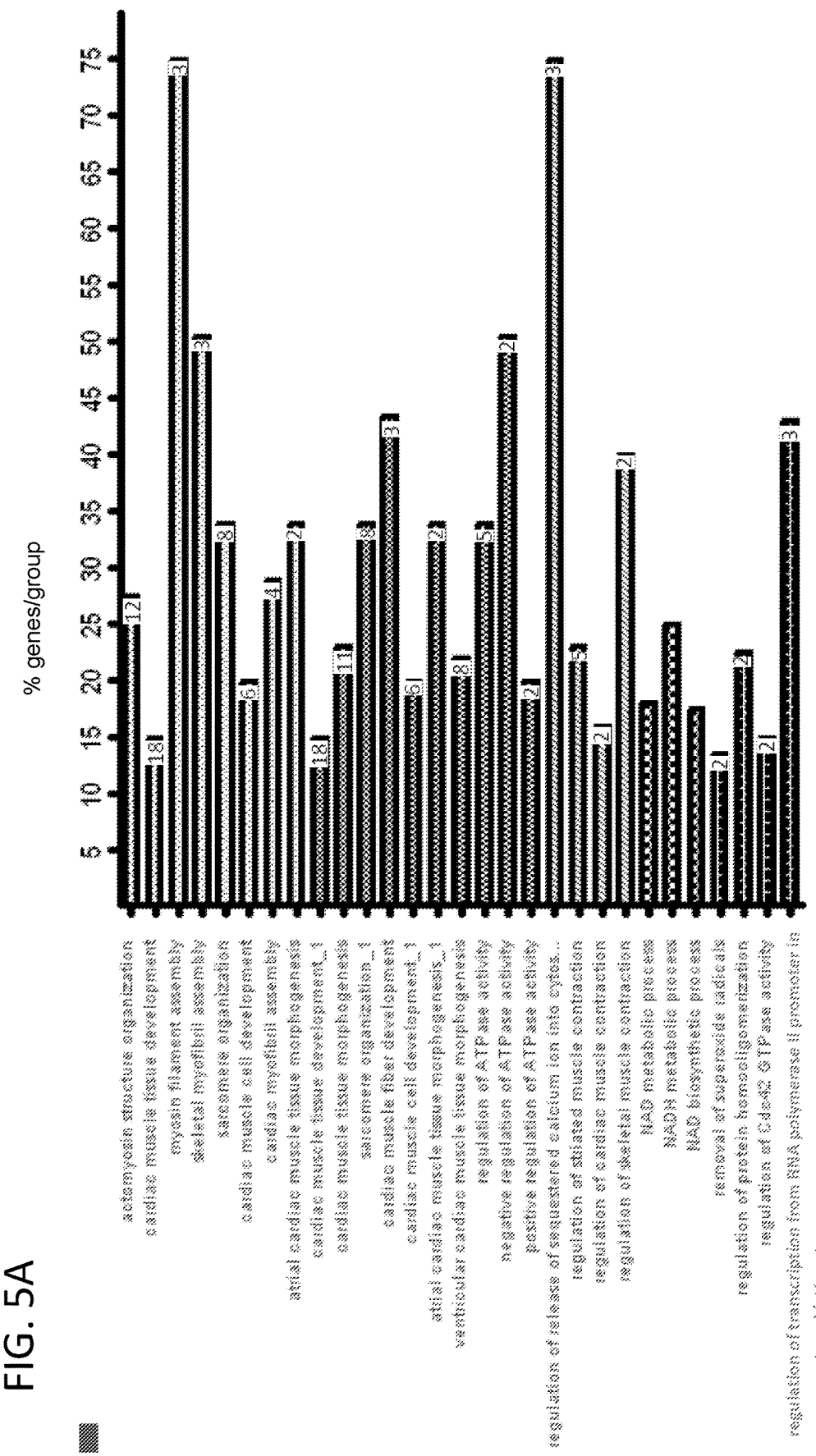
FIG. 5: Transcriptome Status of iSABs Determined by RNA-seq
Figure 5B:
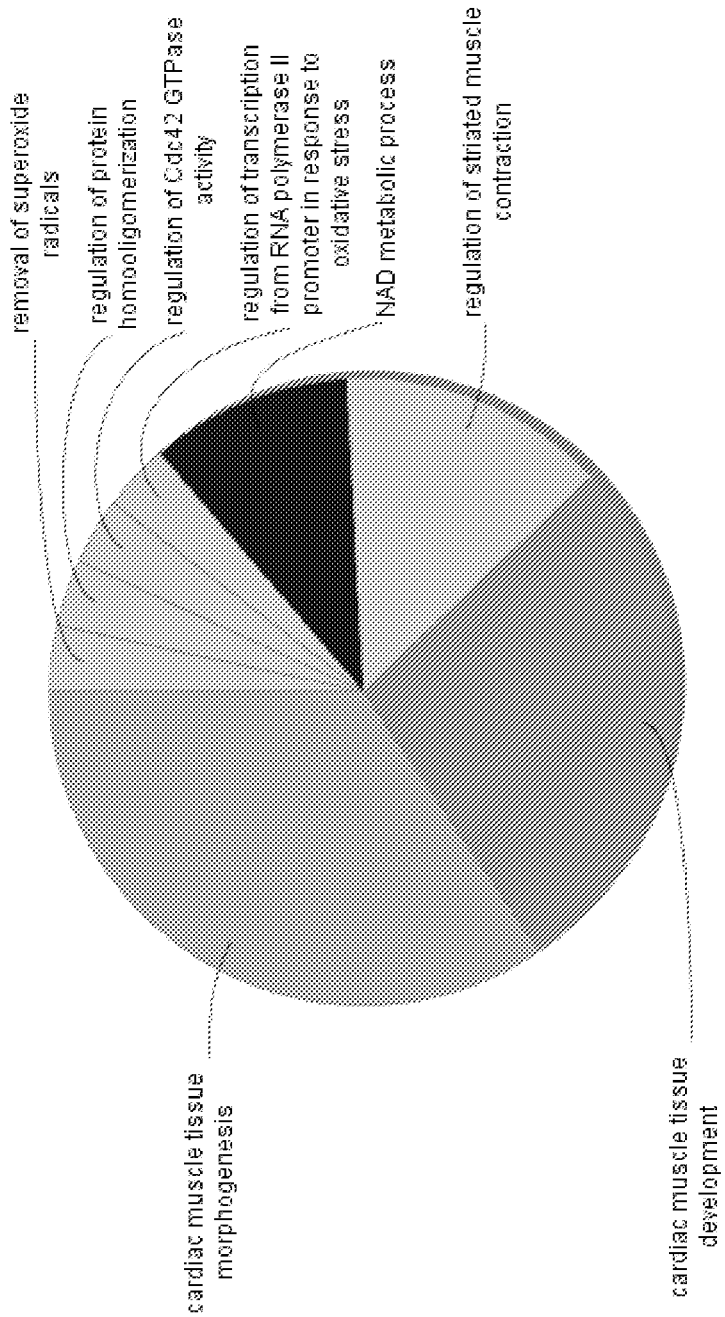
Figure 5C:
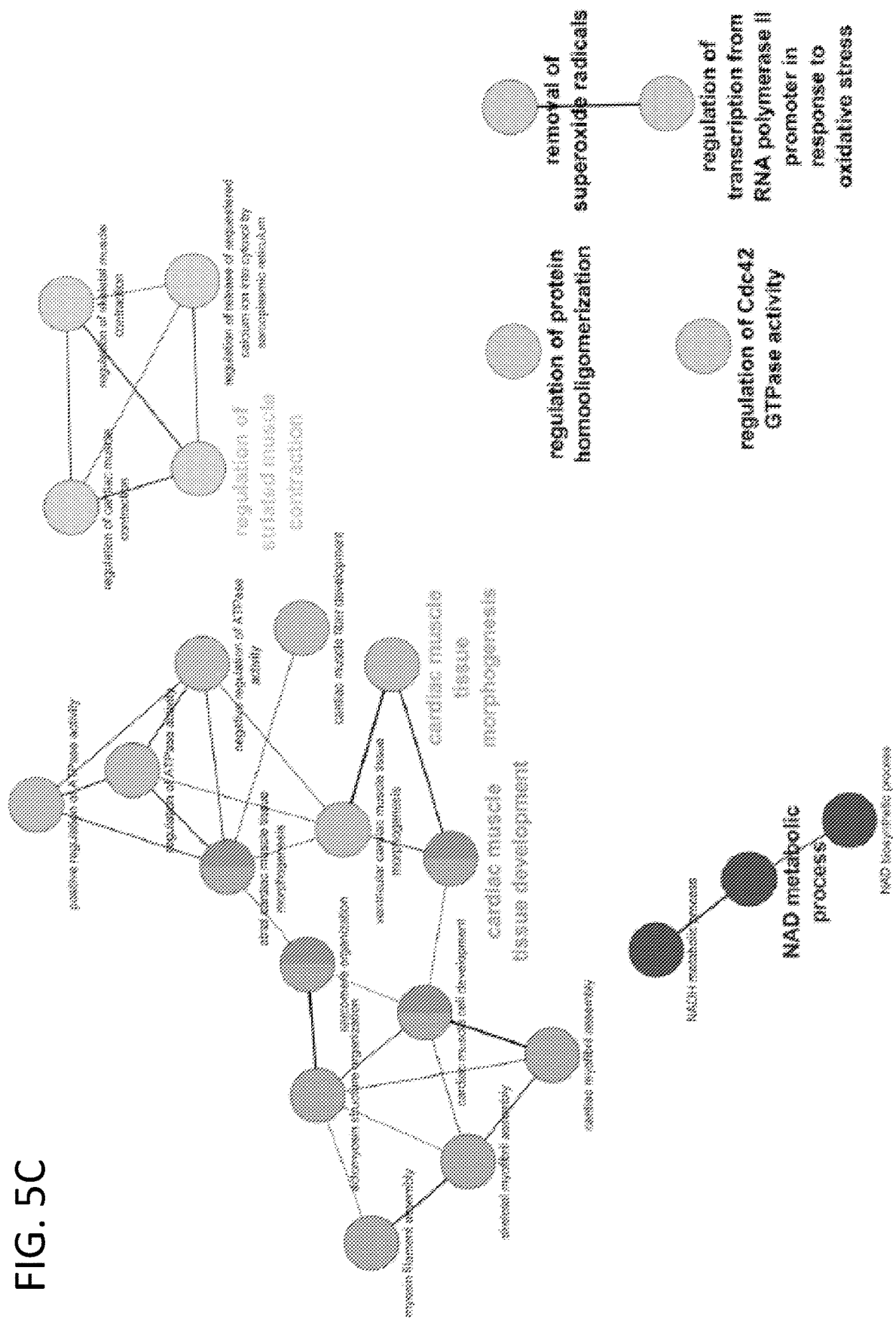
Figure 5D:
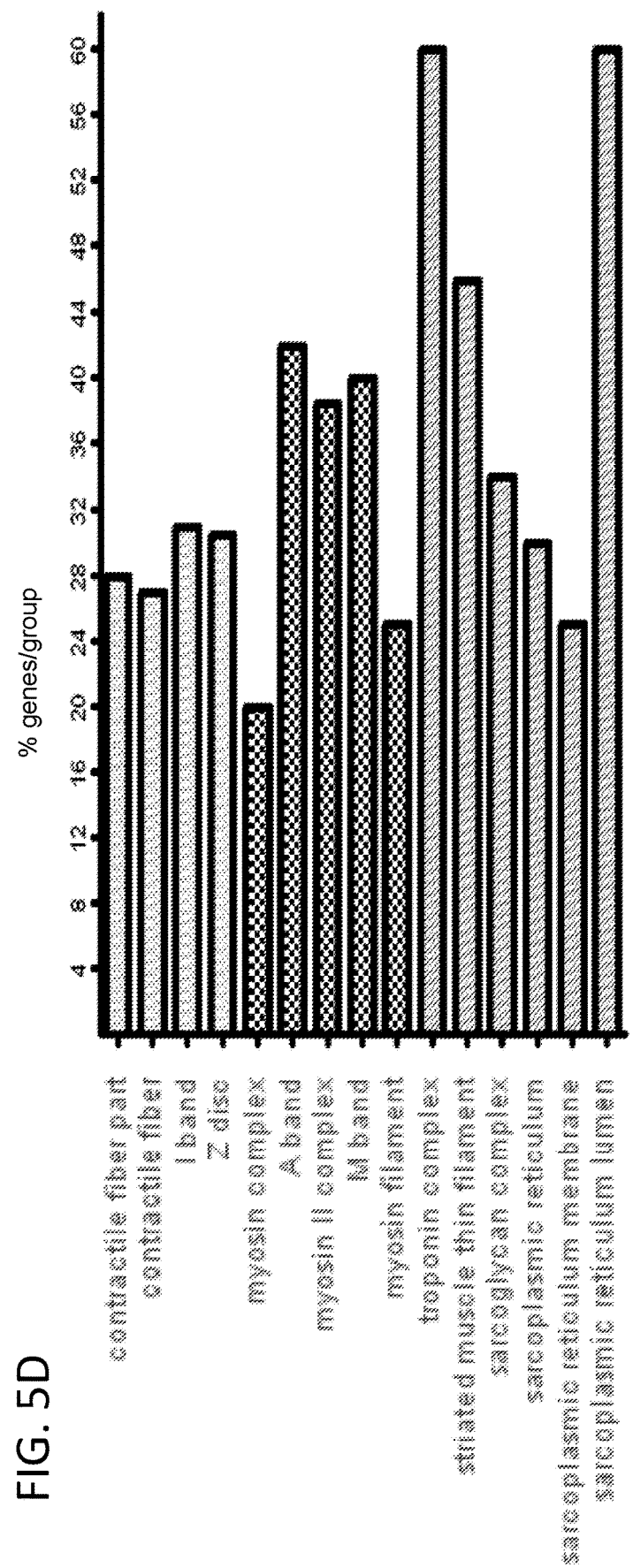
Figure 5E:
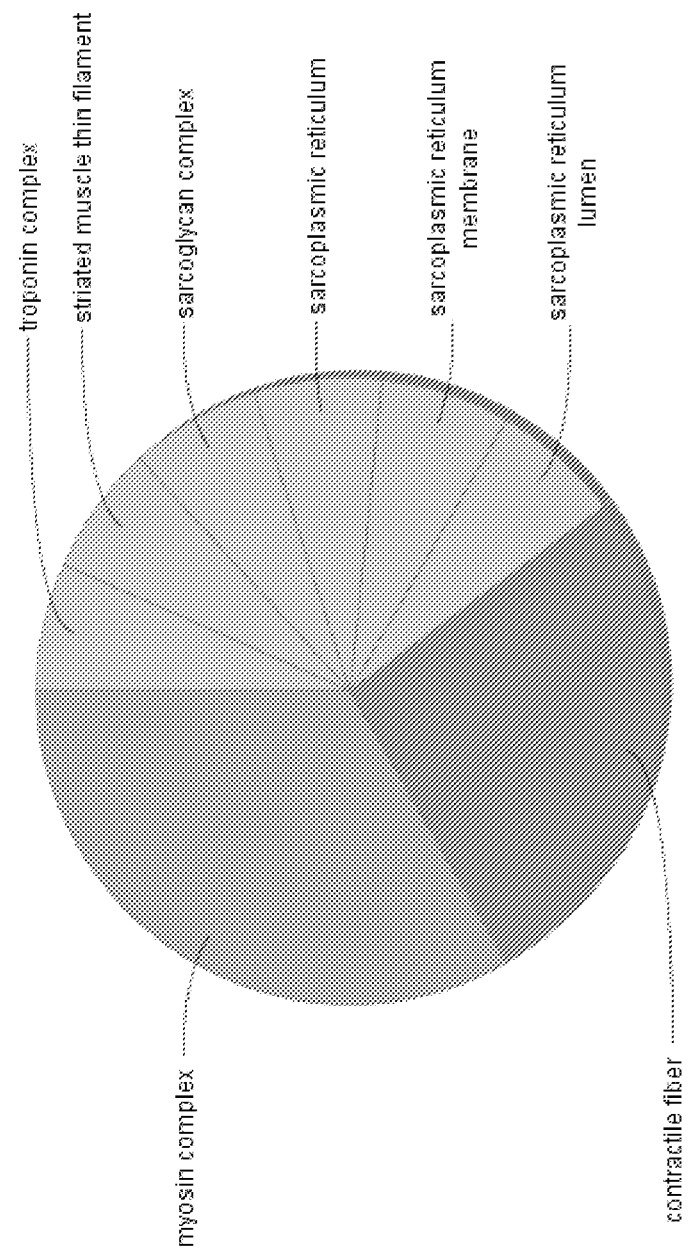
Figure 5F:
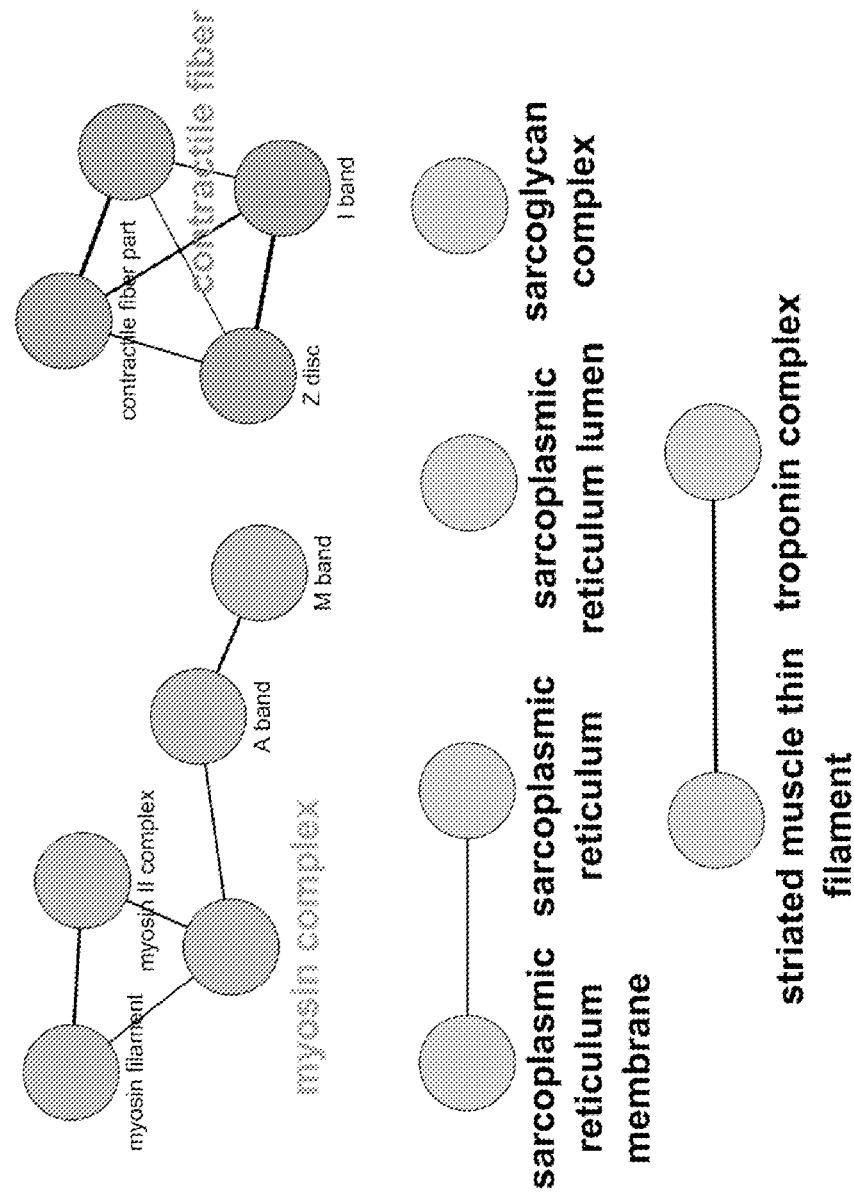
Figure 6B:
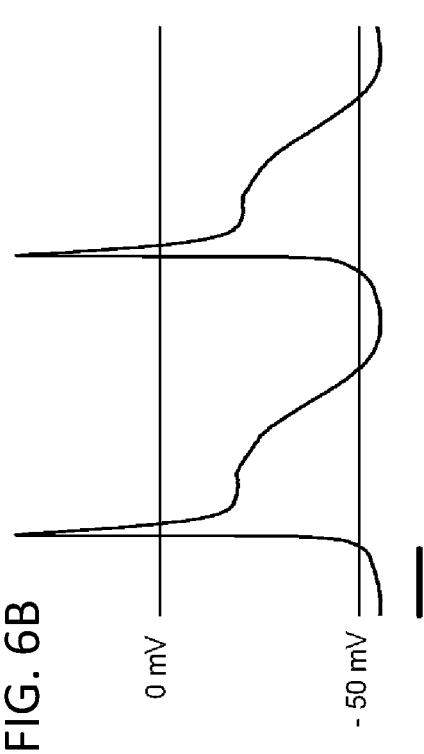
Figure 6D:
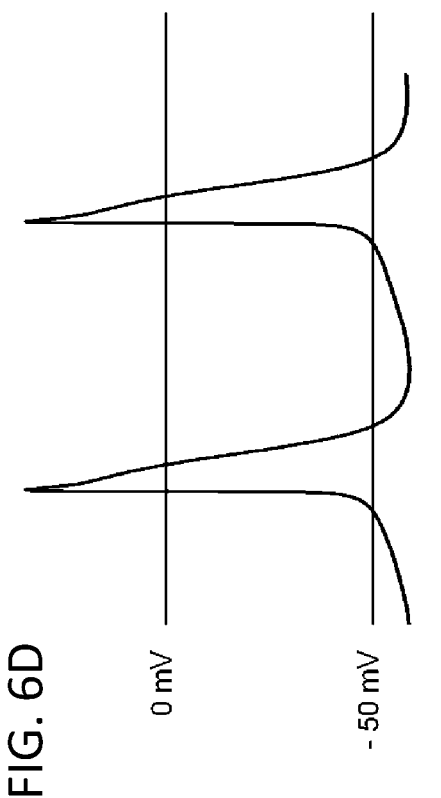
Figure 6A:
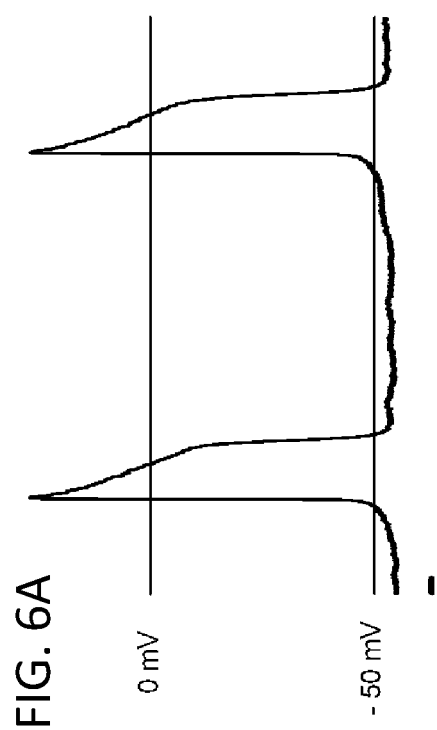
Figure 6C:
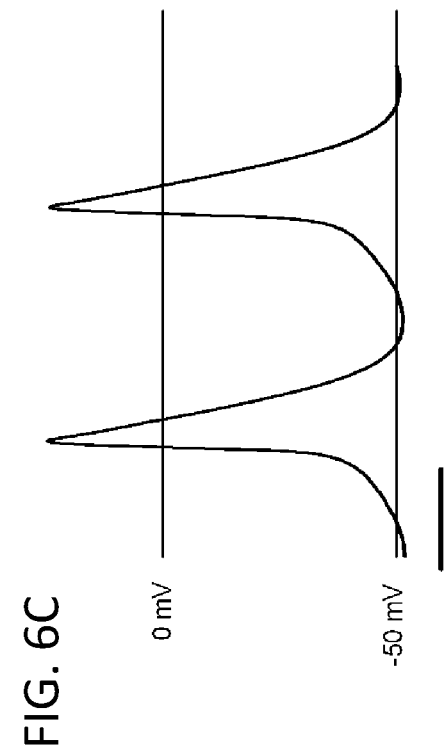
Figure 7A:
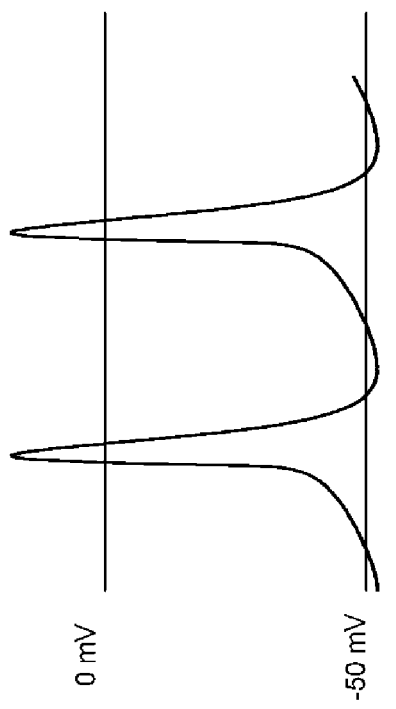
Figure 7B:
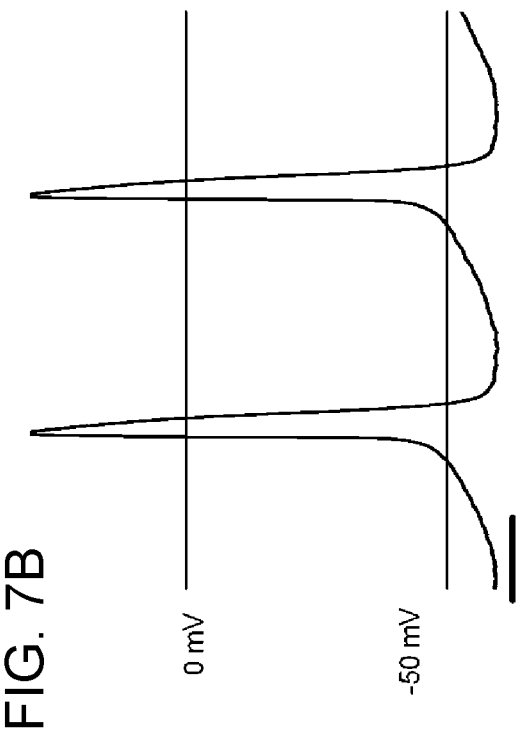

FIG. 7: Representative Action Potentials Obtained From iSAB Cardiomyocytes.

(A) Pacemaker-type action potentials similar to action potentials which have been generated from fully grown murine sinoatrial node cells. (B) Action potentials generated by slightly immature pacemaker-type cells. Horizontal time axis: 100 ms.

FIG. 8: $I_f$ Plots From Isolated iSAB Cells.

(A) Patch-clamp protocol; voltage applied to cause the current activated by hyperpolarization. (B) Example of the $I_f$ current, recorded from an isolated cell originating from an iSAB. (C) Current density and (D) time constant of the activation at −130 mV, showing a robust $I_f$ expression with slow activation kinetics typical of the HCN4 channel subtype and for mature sinoatrial nodes $I_f$, n=17; error bar: mean value±SD.

Figure 9:
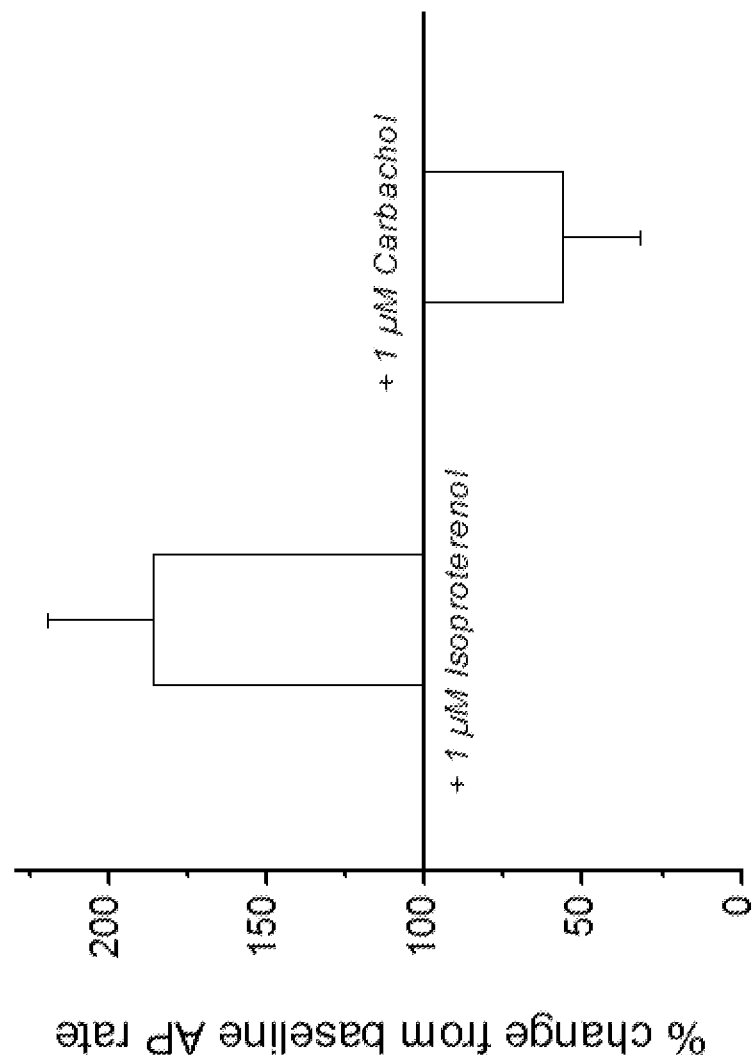

FIG. 9: Modulation of Action Potential (AP) Rates of Isolated Tbx3-Programmed Cells and Cells Originating From iSAB.

Reaction to β-adrenergic (isoprotenerol) and muscarinic (carbachol) stimulation leads to typical accelerated vs. slowed AP rates. Cells originating from iSAB show a clearer response to isoprotenerol with beat frequencies which range up to 560 bpm. iSAB/iso: n=9; iSAB/carb: n=5; error bar: mean value±SD.

FIG. 10: Table 1:Action potential parameters of the cardiomyocytes obtained from action of Tbx3-programmed cells.

The data shown in the table are the mean value ± SD (standard deviation). Commas (,) in the numbers are represented by points (.).

FIG. 11: Table 2: Action potential parameters of cardiomyocytes which have been obtained from iSABs.

The data shown in the table are the mean value ± SD. Commas (,) in the numbers are represented by points(.).

LITERATURE

1. Rosen, M. R., *Biological pacemaking: in our lifetime?* Heart Rhythm., 2005. 2(4): S. 418-28.
2. Ishii, T. M., et al., *Molecular characterization of the hyperpolarization-activated cation channel in rabbit heart sinoatrial node.* J Biol Chem., 1999. 274(18): S. 12835-9.
3. Stieber, J., F. Hofmann, and A. Ludwig, *Pacemaker channels and sinus node arrhythmia.* Trends Cardiovasc Med, 2004. 14(1): S. 23-8.
4. Bakker, M. L., et al., *T-box transcription factor TBX3 reprogrammes mature cardiac myocytes into pacemaker-like cells.* Cardiovasc Res, 2012. 94(3): S. 439-49.
5. Kapoor, N., et al., *Direct conversion of quiescent cardiomyocytes to pacemaker cells by expression of Tbx18.* Nat Biotechnol, 2013. 31(1): S. 54-62.
5a. Hu, Y. -F., et al., *Biological pacemaker created by minimally invasive somatic reprogramming in pigs with complete heart block.* Sci Transl Med, 2014. 245(6): S. 1-10.
6. Wiese, C., et al., *Formation of the sinus node head and differentiation of sinus node myocardium are independently regulated by Tbx18 and Tbx3.* Circ Res, 2009. 104(3): S. 388-97.
7. Wobus, A. M., G. Wallukat, and J. Hescheler, *Pluripotent mouse embryonic stem cells are able to differentiate into cardiomyocytes expressing chronotropic responses to adrenergic and cholinergic agents and Ca2+channel blockers.* Differentiation, 1991. 48(3): S. 173-82.
8. Kehat, I., et al., *High-resolution electrophysiological assessment of human embryonic stem cell-derived cardiomyocytes: a novel in vitro model for the study of conduction.* Circ Res, 2002. 91(8): S. 659-61.
9. Kleger, A., et al., *Modulation of calcium-activated potassium channels induces cardiogenesis of pluripotent stem cells and enrichment of pacemaker-like cells.* Circulation, 2010. 122(18): S. 1823-36.
10. Maltsev, V. A., et al., *Cardiomyocytes differentiated in vitro from embryonic stem cells developmentally express cardiac-specific genes and ionic currents.* Circ Res, 1994. 75(2): S. 233-44.

11. David, R. and W. M. Franz, *From pluripotency to distinct cardiomyocyte subtypes*. Physiology (Bethesda), 2012. 27(3): S. 119-29.
12. Scavone, A., et al., *Embryonic stem cell-derived CD166+ precursors develop into fully functional sinoatrial-like cells*. Circ Res, 2013. 113(4): S. 389-98.
13. David, R., et al., *MesP1 drives vertebrate cardiovascular differentiation through Dkk-1-mediated blockade of Wnt-signalling*. Nat Cell Biol., 2008. 10(3): S. 338-45. Epub 2008 Feb. 24.
14. David, R., et al., *Forward programming of pluripotent stem cells towards distinct cardiovascular cell types*. Cardiovasc Res., 2009. 84(2): S. 263-72. Epub 2009 Jun. 29.
15. Klug, M. G., et al., *Genetically selected cardiomyocytes from differentiating embronic stem cells form stable intracardiac grafts*. J Clin Invest, 1996. 98(1): S. 216-24.
16. David, R., et al., *Selection of a common multipotent cardiovascular stem cell using the 3.4-kb MesP1 promoter fragment*. Basic Res Cardiol, 2013. 108(1): S. 312.
17. Kensah, G., et al., *Murine and human pluripotent stem cell-derived cardiac bodies form contractile myocardial tissue in vitro*. Eur Heart J, 2012. 34(15): S. 1134-46.
18. Otsuji, T. G., et al., *Progressive maturation in contracting cardiomyocytes derived from human embryonic stem cells: Qualitative effects on electrophysiological responses to drugs*. Stem Cell Res, 2010. 4(3): S. 201-13.
19. Kreuzberg, M. M., et al., *Functional properties of mouse connexin30.2 expressed in the conduction system of the heart*. Circ Res, 2005. 96(11): S. 1169-77.
20. Verheijck, E. E., et al., *Electrophysiological features of the mouse sinoatrial node in relation to connexin distribution*. Cardiovasc Res, 2001. 52(1): S. 40-50.
21. Halbach, M., et al., *Ventricular slices of adult mouse hearts—a new multicellular in vitro model for electrophysiological studies*. Cell Physiol Biochem, 2006. 18(1-3): S. 1-8.
22. He, J. Q., et al., *Human embryonic stem cells develop into multiple types of cardiac myocytes: action potential characterization*. Circ Res, 2003. 93(1): S. 32-9.
23. Yanagi, K., et al., *Hyperpolarization-activated cyclic nucleotide-gated channels and T-type calcium channels confer automaticity of embryonic stem cell-derived cardiomyocytes*. Stem Cells, 2007. 25(11): S. 2712-9.
24. Barbuti, A., et al., *Molecular composition and functional properties of f-channels in murine embryonic stem cell-derived pacemaker cells*. J Mol Cell Cardiol, 2009. 46(3): S. 343-51.
25. Ma, J., et al., *High purity human-induced pluripotent stem cell-derived cardiomyocytes: electrophysiological properties of action potentials and ionic currents*. Am J Physiol Heart Circ Physiol, 2011. 301(5): S. H2006-17.
26. Morikawa, K., et al., *Identification, isolation and characterization of HCN4-positive pacemaking cells derived from murine embryonic stem cells during cardiac differentiation*. Pacing Clin Electrophysiol, 2010. 33(3): S. 290-303.
27. Garcia-Frigola, C., Y. Shi, and S. M. Evans, *Expression of the hyperpolarization-activated cyclic nucleotide-gated cation channel HCN4 during mouse heart development*. Gene Expr Patterns, 2003. 3(6): S. 777-83.
28. Wiese, C., et al., *Differentiation induction of mouse embryonic stem cells into sinus node-like cells by suramin*. Int J Cardiol, 2011. 147(1): S. 95-111.
29. Johns, D. C., et al., *Adenovirus-mediated expression of a voltage-gated potassium channel in vitro (rat cardiac myocytes) and in vivo (rat liver). A novel strategy for modifying excitability*. J Clin Invest, 1995. 96(2): S. 1152-8.
30. Nuss, H. B., E. Marban, and D. C. Johns, *Overexpression of a human potassium channel suppresses cardiac hyperexcitability in rabbit ventricular myocytes*. J Clin Invest, 1999. 103(6): S. 889-96.
31. Evans, M. J. and M. H. Kaufman, *Establishment in culture of pluripotential cells from mouse embryos*. Nature, 1981. 292(5819): S. 154-6.
32. Martin, G. R., *Isolation of a pluripotent cell line from early mouse embryos cultured in medium conditioned by teratocarcinoma stem cells*. Proc Natl Acad Sci USA, 1981. 78(12): S. 7634-8.
33. Gerecht-Nir, S., B. Fishman, and J. Itskovitz-Eldor, *Cardiovascular potential of embryonic stem cells*. Anat Rec A Discov Mol Cell Evol Biol, 2004. 276(1): S. 58-65.
34. Takahashi, K. and S. Yamanaka, *Induction of pluripotent stem cells from mouse embryonic and adult fibroblast cultures by defined factors*. Cell., 2006. 126(4): S. 663-76. Epub 2006 Aug. 10.
35. Takahashi, K., et al., *Induction of pluripotent stem cells from adult human fibroblasts by defined factors*. Cell., 2007. 131(5): S. 861-72.
36. Mauritz, C., et al., *Generation of functional murine cardiac myocytes from induced pluripotent stem cells*. Circulation., 2008. 118(5): S. 507-17. Epub 2008 Jul. 14.
37. David, R., M. Groebner, and W. M. Franz, *Magnetic cell sorting purification of differentiated embryonic stem cells stably expressing truncated human CD4 as surface marker*. Stem Cells, 2005. 23(4): S. 477-82.
38. Trapnell, C., L. Pachter, and S. L. Salzberg, *TopHat: discovering splice junctions with RNA-Seq*. Bioinformatics, 2009. 25(9): S. 1105-11.
39. Anders, S. and W. Huber, *Differential expression analysis for sequence count data*. Genome Biol, 2010. 11(10): S. R106.
40. Goecks, J., A. Nekrutenko, and J. Taylor, *Galaxy: a comprehensive approach for supporting accessible, reproducible, and transparent computational research in the life sciences*. Genome Biol, 2010. 11(8): S. R86.

The invention claimed is:

1. A method of producing sinoatrial node cells from human stem cells, the method comprising the steps of:
    (A) introducing a nucleic acid into the stem cells, wherein the nucleic acid encodes a TBX3 transcription factor, or introducing a TBX3 protein into the stem cells to generate TBX3-overexpressing stem cells;
    (B) introducing a nucleic acid into the TBX3-overexpressing stem cells, wherein the nucleic acid encodes an antibiotic resistance gene under the control of an alpha-MHC (MYH6) promoter;
    (C) after introducing the nucleic acid encoding an antibiotic resistance gene under the control of an MYH6 promoter in step (B), culturing the TBX3-overexpressing stem cells under conditions in which the antibiotic resistance gene is expressed;
    (D) culturing the cells of step (C) with an antibiotic to which the cells expressing the antibiotic resistance gene are resistant;
    (E) selecting antibiotic-resistant Myh6-TBX3 cells; and
    (F) differentiating the antibiotic-resistant Myh6-TBX3 cells from step
    (E) into sinoatrial node cells having 50 to 90 action potentials per minute.
2. The method of producing sinoatrial node cells from stem cells according to claim 1, wherein the sinoatrial node cells are comprised in cell aggregates consisting of spontaneous beating cardiomyocytes (KM cells) and more than 60% of the KM cells are sinoatrial node cells.

3. The method of producing sinoatrial node cells from stem cells according to claim 1, wherein multipotent or pluripotent stem cells are used.

4. The method of producing sinoatrial node cells from stem cells according to claim 1, wherein human embryonic stem cells, human induced stem cells, human parthenogenetic stem cell, or human spermatogonial stem cells are used.

5. The method of producing sinoatrial node cells from stem cells according to claim 1, wherein the nucleic acid is TBX3 DNA.

6. The method of producing sinoatrial node cells from stem cells according to claim 1, wherein the introduction of the TBX3 nucleic acid is effected by means of a vector.

7. The method of producing sinoatrial node cells from stem cells according to claim 1, wherein the antibiotic resistance gene is an aminoglycoside antibiotic resistance gene and the antibiotic is an aminoglycoside antibiotic.

8. A method of producing sinoatrial node cells from murine stem cells, the method comprising the steps of:
(A) introducing a nucleic acid into the stem cells, wherein the nucleic acid encodes a TBX3 transcription factor, or introducing a TBX3 protein into the stem cells to generate TBX3-overexpressing stem cells;
(B) introducing a nucleic acid into the TBX3-overexpressing stem cells, wherein the nucleic acid encodes an antibiotic resistance gene under the control of an alpha-MHC (MYH6) promoter;
(C) after introducing the nucleic acid encoding an antibiotic resistance gene under the control of an MYH6 promoter in step (B), culturing the TBX3-overexpressing stem cells under conditions in which the antibiotic resistance gene is expressed;
(D) culturing the cells of step (C) with an antibiotic to which the cells expressing the antibiotic resistance gene are resistant;
(E) selecting antibiotic-resistant Myh6-TBX3 cells; and
(F) differentiating the antibiotic-resistant Myh6-TBX3 cells from step (E) into sinoatrial node cells having 300 to 700 action potentials per minute.

9. The method of producing sinoatrial node cells from stem cells according to claim 8, wherein the sinoatrial node cells are comprised in cell aggregates consisting of spontaneous beating cardiomyocytes (KM cells) and more than 60% of the KM cells are sinoatrial node cells.

10. The method of producing sinoatrial node cells from stem cells according to claim 8, wherein multipotent or pluripotent stem cells are used.

11. The method of producing sinoatrial node cells from stem cells according to claim 8, wherein the nucleic acid is TBX3 DNA.

12. The method of producing sinoatrial node cells from stem cells according to claim 8, wherein the introduction of the TBX3 nucleic acid is effected by means of a vector.

13. The method of producing sinoatrial node cells from stem cells according to claim 8, wherein the antibiotic resistance gene is an aminoglycoside antibiotic resistance gene and the antibiotic is an aminoglycoside antibiotic.

14. The method of producing sinoatrial node cells from stem cells according to claim 8, wherein murine embryonic stem cells, murine induced stem cells, murine parthenogenetic stem cell, or murine spermatogonial stem cells are used.

* * * * *